(12) United States Patent
Vecchio et al.

(10) Patent No.: US 11,135,445 B2
(45) Date of Patent: *Oct. 5, 2021

(54) ANTIMICROBIAL PHOTODYNAMIC INACTIVATION PROCEDURE AND SYSTEM

(71) Applicant: The General Hospital Corporation, Boston, MA (US)

(72) Inventors: Daniela Vecchio, Cambridge, MA (US); Michael R. Hamblin, Boston, MA (US); Yingying Huang, Boston, MA (US); Liyi Huang, Boston, MA (US); Giacomo Landi, Cambridge, MA (US); Jeffrey A. Gelfand, Boston, MA (US); Timothy Brauns, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 270 days.

This patent is subject to a terminal disclaimer.

(21) Appl. No.: 16/277,191

(22) Filed: Feb. 15, 2019

(65) Prior Publication Data
US 2019/0175933 A1 Jun. 13, 2019

Related U.S. Application Data

(63) Continuation-in-part of application No. 15/528,015, filed as application No. PCT/US2015/061328 on Nov. 18, 2015, now Pat. No. 10,780,294.
(Continued)

(51) Int. Cl.
*A61N 5/06* (2006.01)
*A61B 18/24* (2006.01)
(Continued)

(52) U.S. Cl.
CPC .............. *A61N 5/062* (2013.01); *A61B 18/24* (2013.01); *A61K 31/045* (2013.01); *A61K 31/43* (2013.01);
(Continued)

(58) Field of Classification Search
CPC ........................... A61K 41/0057; A61N 5/062
See application file for complete search history.

(56) References Cited

U.S. PATENT DOCUMENTS 4,320,140 A * 3/1982 Crounse ................. A01N 43/16
514/454

OTHER PUBLICATIONS

Wen X, Zhang X, Szewczyk G, El-Hussein A, Huang Y-Y, Sarna T, Hamblin MR. Potassium iodide potentiates antimicrobial photodynamic inactivation, Antimicrobial Agents and Chemotherapy, vol. 6, Iss. 7, 2017. (Year: 2017).*

* cited by examiner

*Primary Examiner* — Laura A Bouchelle
(74) *Attorney, Agent, or Firm* — Yakov Sidorin; Quarles & Brady LLP

(57) ABSTRACT

A problem of incomplete inhibition of harmful cells/bacteria and short duration of time, after the photodynamic treatment, during which such cells may re-grow, is solved by exposing the target bacteria with a multi-component photosensitizer material formed by adding a predetermined potentiating chemical to a conventional single-component photosensitizer at the target, prior to irradiating the target with light. The multi-component photosensitizer is effectuated by forming a mix of the two chemical compositions or by sequential exposure of the bacteria to a single-component photosensitizer and the potentiating chemical of choice.

11 Claims, 26 Drawing Sheets

Related U.S. Application Data

(60) Provisional application No. 62/081,636, filed on Nov. 19, 2014, provisional application No. 62/632,297, filed on Feb. 19, 2018.

(51) Int. Cl.
  *A61K 41/00* (2020.01)
  *A61K 41/17* (2020.01)
  *A61K 31/045* (2006.01)
  *A61K 31/43* (2006.01)
  *G02B 23/26* (2006.01)

(52) U.S. Cl.
  CPC .......... *A61K 41/0057* (2013.01); *A61K 41/17* (2020.01); *A61N 5/0624* (2013.01); *G02B 23/26* (2013.01)

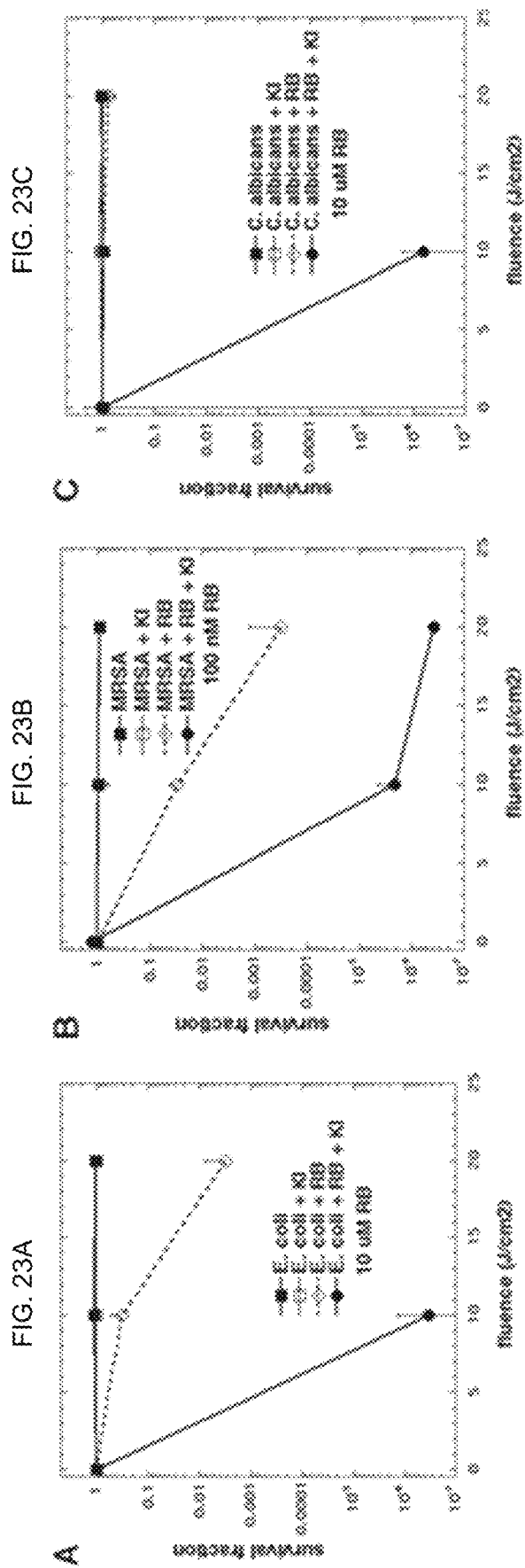

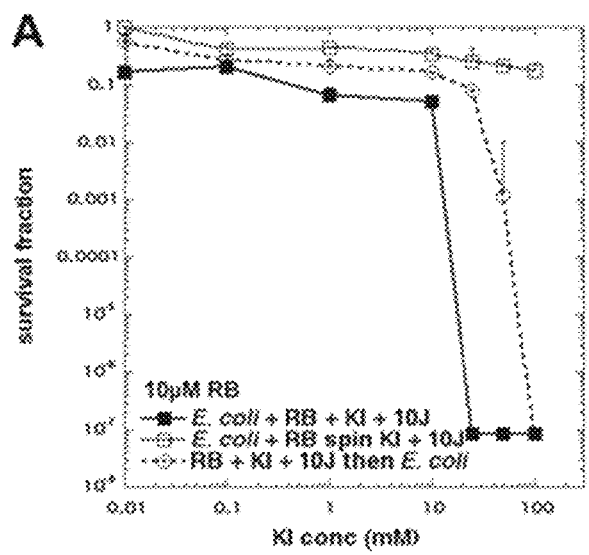
FIG. 24A
FIG. 24B
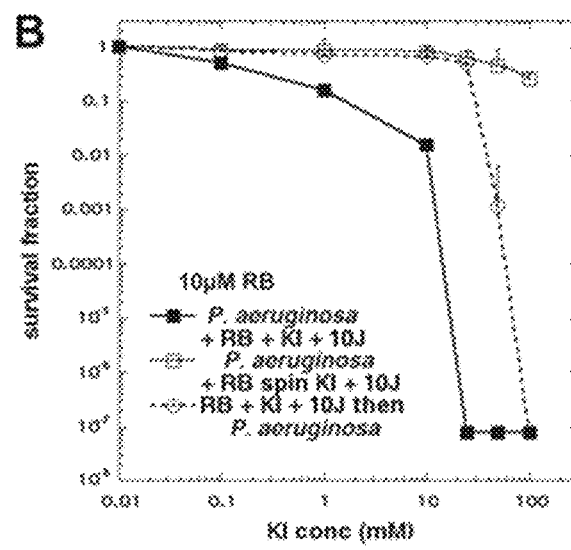
FIG. 24C
FIG. 24D
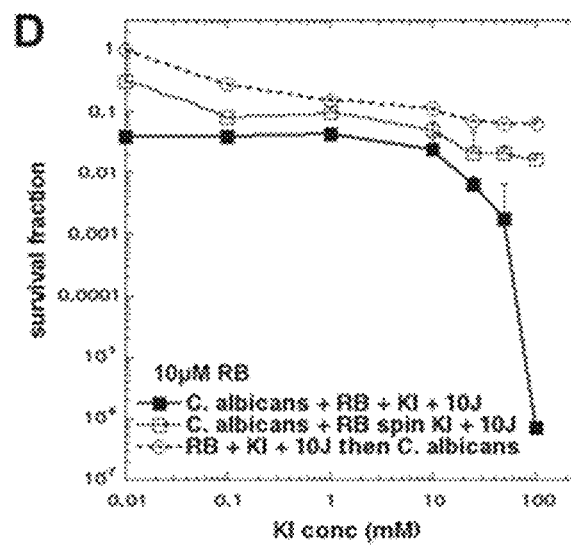

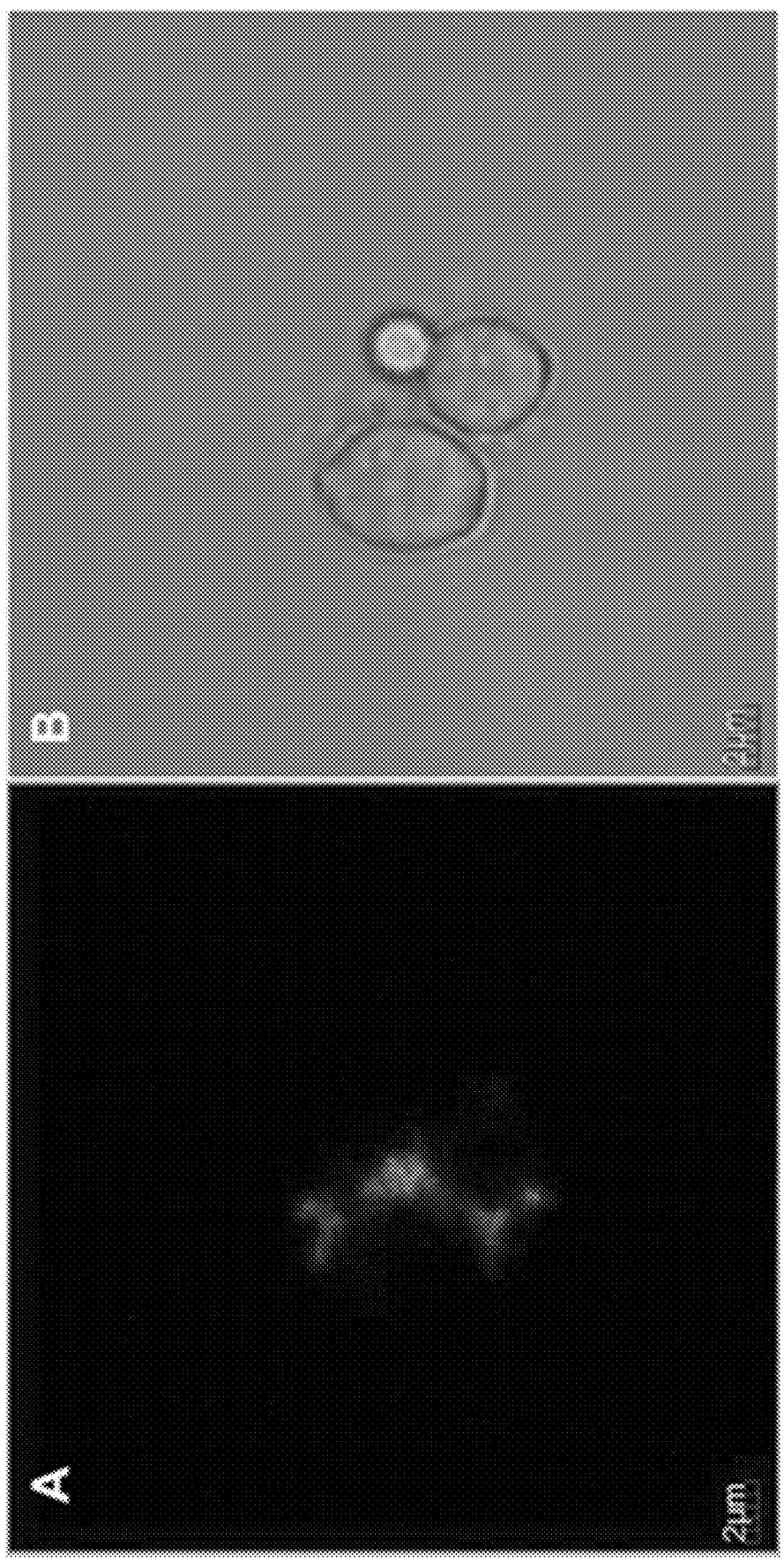

ANTIMICROBIAL PHOTODYNAMIC INACTIVATION PROCEDURE AND SYSTEM

CROSS-REFERENCE TO RELATED APPLICATIONS

The present application claims priority from the U.S. Provisional Patent Application No. 62/632,297, filed on Feb. 19, 2018. The present application is also a continuation-in-part from the U.S. patent application Ser. No. 15/528,015, filed on May 18, 2017 and now published as US2018/0036552, which in turn is the US National Stage of International Application No. PCT/US2015/061328, filed Nov. 18, 2015, which in turn claims priority from the U.S. Provisional Patent Application No. 62/081,636 filed on Nov. 19, 2014. The disclosure of each of the above-identified patent documents is incorporated herein by reference.

TECHNICAL FIELD

This invention is related to systems and methods utilizing species producing antimicrobial effects and, in particular, to increase of efficiency of a process of photodynamic inactivation of target bacteria mediated by a single-component photosensitizer with the use of a pre-determined potentiating composition of matter.

RELATED ART

The ever-growing spread of resistance of microbes to antibiotics urges the search for antimicrobial methodologies to which microbes may be unable to develop resistance. Photodynamic inactivation (PDI) is a methodology developed to kill multidrug-resistant microorganisms with the use of the combination of a single-component non-toxic material (termed a photosensitizer, or PS) and harmless to the biological tissue visible light. Conventionally, the PDI process employs a PS in the form of a single-component non-toxic dye together with irradiation of such PS with low intensity visible light. In the presence of oxygen, light induces the formation of reactive oxidative species (ROS), which are generated by energy- or electron transfer from the PS long-lived triplet excited state that are able to oxidize biomolecules and thereby kill microbial cells.

The photochemistry from the PS triplet state can occur along two parallel pathways: Type 1 involves electron transfer to oxygen, initially forming superoxide and eventual production of cytotoxic hydroxyl radicals; while Type 2 involves energy transfer to ground state oxygen and production of cytotoxic singlet oxygen. It is known that selectivity of the PS for bacteria over host medium can be obtained by the appropriate chemical design to ensure that the PS molecule preferentially binds to the bacterial cells.

Although various advances in chemical design of new PS's have been made, the dye-based PS's have some practical limitations leading to recurrence and/or regeneration of harmful bacteria after the irradiation of the PS has been completed. The thus-far attempted chemical enhancement(s) of the conventionally-used methylene blue (MB) remained impractical due to the toxicity of the resulting compound(s).

SUMMARY

Embodiments of the invention provide a method for photodynamic inactivation of target bacteria. The method includes a step of treating the target bacteria to form a first amount of treated bacteria by establishing contact between first and second compositions of matter and the target bacteria. The first composition of matter includes a single-component photosensitizer (PS) having a first efficiency in mediating the process on its own, while the second composition of matter has no efficiency in mediating the process on its own. Generally, the step of treating includes establishing contact between the target bacteria and the first composition of matter including one of methylene blue, toluidine blue, new methylene blue, dimethyl-methylene blue, Nile blue derivative material, fullerene, rose Bengal, and titania, and establishing contact between the living bacteria and the second composition of matter including at least one of an iodide salt of an alkaline metal, a nitrite salt of an alkaline metal, a thiocyanate salt of an alkaline metal, a selenocyanate sale of an alkaline metal, and a bromide salt of an alkaline metal.

The method further includes a step of irradiating the first amount of treated bacteria, for a pre-determined duration of time, with light having a chosen wavelength to reduce the first amount of treated bacteria. The chosen wavelength is determined such that light at the chosen wavelength triggers the process of photodynamic inactivation when the target bacteria has been treated with only the single-component PS. The method may further include intermixing the first and second compositions of matter prior to the step of treating the living bacteria and, in a specific case, intermixing a first solution of the first composition of matter and a second solution of the second composition of matter. Solutions may be aqueous solutions.

The step of treating, in one implementation, includes sequentially applying the first and second compositions of matter to the living bacteria, and can be implemented when the first composition of matter is already carried by a support surface. As a result of such sequential application, the first amount is reduced by a factor of K>L; here, L is a factor of reduction of a second amount of treated bacteria as a result of irradiating a second amount of treated bacteria with said light for said pre-determined duration of time, and the second amount of treated bacteria is an amount formed as a result of establishing contact between a mixture of the first and second compositions of matter and said target bacteria.

For example, the step of treating includes establishing contact between the first and second compositions of matter and the target bacteria carried by a surface of at least one of a dental tool (such as a dental implant or a titanium dioxide nanotubes incorporated into a filling for teeth, for example), a surgical tool, and a surface in a clinical environment. In one embodiment, the step of irradiating includes reducing the first amount of treated bacteria by a factor of M>N. Here, N is a factor of reduction of a second amount of treated bacteria as a result of irradiating a second amount of treated bacteria with the same light for the same pre-determined duration of time, while the second amount of treated bacteria is an amount formed as a result of establishing contact between only the first composition of matter and the target bacteria. M/N is at least 10; preferably at least 100; more preferably at least 1,000; and even more preferably, at least 10,000.

In a related embodiment, the step of treating includes transporting at least one of the first and second compositions of matter along a delivery channel of a catheter to a distal portion of the catheter, while the step of irradiating includes transmitting such light along a body of the catheter and, in particular, in an optical waveguide disposed within a wall of the catheter to the treated bacteria disposed near the distal portion of the catheter.

BRIEF DESCRIPTION OF DRAWINGS

The invention will be more fully understood by referring to the following Detailed Description of Specific Embodiments in conjunction with the generally not-to-scale Drawings, of which:

(FIGS. 6B, 6D);

FIG. 11A: $TiO_2$ 1 mM on MRSA (10(8) cells/mL); FIG. 11B: $TiO_2$ 5 mM on MRSA (10(8) cells/mL); FIG. 11C: $TiO_2$ 1 mM on *E. coli* (10(8) cells/mL); FIG. 11D: $TiO_2$ 5 mM on *E. coli* (10(8) cells/mL); FIG. 11E: $TiO_2$ 5 mM on *C. albicans* (10(7) cells/mL). Values are means of 3 repetitions and bars are SD.

FIG. 13A: SOSG; FIG. 13B: HPF. Values are means of 6 wells and bars are SD.

FIG. 14A: absorbance of $I_2$ at 350 nM; FIG. 14B: absorbance spectrum of $I_2$. Values are means of 3 repetitions and bars are SD;

FIGS. 23A, 23B, 23C illustrated effect of KI on light dose-dependent aPDI. Cells were incubated for 30 min with RB (at the specified concentration) plus 100 mM KI, and then 540-nm light was delivered (0, 10, or 20 J/cm$^2$). Controls were cells alone or cells incubated with KI alone. FIG. 23A: Gram-negative bacterium *E. coli*; FIG. 23B: Gram-positive bacterium MRSA; FIG. 23C fungal yeast *C. albicans*.

FIGS. 24A, 24B, 24C, 24D illustrate effect of spin and addition sequence on RB plus KI aPDI. RB (10 μM for Gram-negative bacteria and fungi or 100 nM for MRSA) was exposed to 10 J/cm$^2$ of 540-nm light in the presence of different concentrations of KI. Cells (10$^8$/ml for bacteria or 10$^7$/ml for fungi) were either present during light, centrifuged before addition of KI and light, or added after light. Controls (light alone or light plus KI) showed no loss of viability (data not shown). FIG. 24A: Gram-negative bacterium *E. coli*; FIG. 24B: Gram-negative bacterium *P. aeruginosa*; FIG. 24C: Gram-positive bacterium MRSA; FIG. 24D: fungal yeast *C. albicans*.

FIGS. 25A, 25B display confocal images of *C. albicans* incubated with RB (10 μM) for 30 min and centrifuged. FIG. 25A: Emission at 585 nm; FIG. 25B: a grayscale image.

FIG. 26A: Production of iodine (measured as blue starch complex) by RB+KI+green light; FIG. 26B: production of hydrogen peroxide (measured by Amplex Red assay) by RB+KI+green light; FIG. 26C: lack of production of superoxide (measured by nitroblue tetrazolium assay) by RB+KI+green light; fullerene+NADH+360-nm light was used as positive (+ve) control. AU, absorbance units.

FIG. 27A: Activation of SOSG by RB (100 nM) excited by 540-nm light with and without added KI (100 mM); FIG. 27B: time-resolved kinetics of the formation and decay of 1,270-nm phosphorescence detected in the presence and absence of 35 mM KI; FIG. 27C: lifetime of singlet oxygen and its initial intensity as a function of the KI concentration.

FIGS. 31A and 31E: No-treatment control; FIGS. 31B and 31F: mix of RB and KI in the dark; FIGS. 31C and 31G: RB plus irradiation with light; FIGS. 31D and 31H: mix of RB and KI and irradiation with light; FIGS. 31A to 31D: Gram stain; FIGS. 31E to 31H: H&E stain. Bar, 100 μm.

Figure 1A:
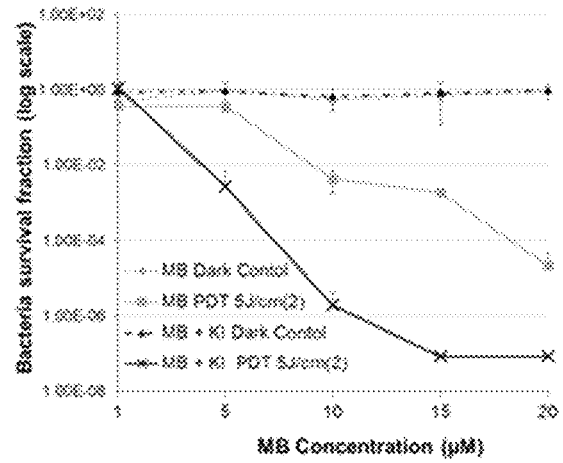
FIGS. 1A, 1B, 1C present plots illustrating results of potentiation of MB-antibacterial PDI by addition of potassium iodide, in vitro, with respect to *S. aureus;*

Generally, the Drawings provide schematic depictions only, and the sizes and relative scales of elements in Drawings may be set to be different from actual ones to appropriately facilitate simplicity, clarity, and understanding of the Drawings. For the same reason, not all elements present in one Drawing may necessarily be shown in another.

DETAILED DESCRIPTION

The idea of the invention stems from the realization that both a photodynamic potency of the PDI of the harmful cells at the target and the duration of time during which, after the PDI treatment, the bacteria does not reappear can be significantly increased (as compared with that of a conventional PDI process) by utilizing either (i) a treatment of the target with a complex, multi-component PS (that includes a practical combination, or aggregation of chosen chemical(s) intermixed with a known single-component PS, in a judiciously predetermined ratio) or (ii) a sequential treatment of the target with the components of a pre-determined multi-component PS (that is, a sequential treatment of the target with a known single-component PS and the chosen chemical(s)).

The problems of practically incomplete effects produced by a conventional PDI process—specifically, incomplete inhibition of harmful cells/bacteria and short duration of time, after the PDI treatment, during which such cells may re-grow—are solved by judiciously treating the target living bacteria with a multi-component PS material (referred to hereinafter as MCPPS) that is formed by operationally adding a predetermined potentiating chemical to a conventional, single-component PS at the target, prior to applying light to initiate photochemistry required for the PDI process to take effect. The operational, practical addition of the potentiating chemical component to the single-component PS can be carried out by forming a mix of these two chemical compositions (with which mix the target living bacteria is then treated) or, alternatively, by sequentially treating the bacteria with a single-component PS and the potentiating chemical of choice.

According to the idea of the invention, the potentiating chemicals are specifically defined or chosen such that, when the MCPPS combination material is irradiated with light at wavelengths tailored to activate the single-component PS in the MCPPS material, the MCPPS material generates reactive inorganic radicals (in a specific case—through Type 1 electron transfer, for example), while in absence of triggering light the generation of such radicals remains substantially non-existent. Furthermore, the MCPPS is designed such that—in stark contradistinction with at least single-component PS's of related art—the MCPPS is not only non-toxic but, when used for strengthening and increasing the efficiency of the PDI process, prevents recurrence/regeneration of biological species targeted in the PDI process. In addition, the components of the MCPPS are formulated such as to cause the PDI process to be selective, in that only the targeted biological species are affected and not the ambient environment hosting these species.

Non-limiting examples of the components of the MCPPS formulated according to the idea of the invention include those shown in Table 1.

TABLE 1

| Single-component PS | Wavelength of Activating Light | Potentiating Chemical |
| --- | --- | --- |
| Methylene blue (MB) | 660 nm | Iodide salt (such as, e.g., KI, NaI) |
| Toluidine blue (TB) | 630 nm | Nitrite salt (such as, e.g., $KNO_2$, $NaNO_2$) |
| New methylene blue (NMB) | 660 nm | Thiocyanate salt (such as, e.g., KSCN, NaSCN) |
| Dimethyl-methylene blue (DMB) | 630 nm | Selenocyanate salt (such as, e.g., KSeCN, NaSeCN) |
| Nile blue derivative (EtNBS) | 660 nm | Bromide salt (KBr, NaBr) |
| Rose Bengal (RB) | 540 nm | Iodide salt (such as, e.g., KI, NaI) |

Some additional, non-limiting types of a conventional, single-component PS that are potentiated according to the idea of the invention include Azure A (activated at about 650 nm), Azure AB (activated at about 640 nm), Azure C (activated at about 630 nm), thionin (activated at about 600 nm), Riboflavin (activated at 360 nm, 440 nm), titanium dioxide (referred to as titania, activated at 360 nm), copper phthalocyhanine (activated at 670 nm), cationic fullerenes (activated at 360 nm, 415 nm, or with broadband/white light).

According to the idea of the invention, the target living bacteria can be treated with an MCPPS that is formed by combining of any of the single-component PS materials listed in Table 1 or mentioned right after with any of the potentiating chemical listed in Table 1.

For example, combinations of MCPPS-components include: MB and an iodide (or nitrite, or thiocyanate, or selenocyanate, or bromide) salt of alkaline metal; TB and an iodide (or nitrite, or thiocyanate, or selenocyanate, or bromide) salt of alkaline metal; NMB and an iodide (or nitrite, or thiocyanate, or selenocyanate, or bromide) salt of alkaline metal; DMB and an iodide (or nitrite, or thiocyanate, or selenocyanate, or bromide) salt of alkaline metal; EtNBS and an iodide (or nitrite, or thiocyanate, or selenocyanate, or bromide) salt of alkaline metal; titanium dioxide and an iodide (or nitrite, or thiocyanate, or selenocyanate, or bromide) salt of alkaline metal; cationic fullerenes and an iodide (or nitrite, or thiocyanate, or selenocyanate, or bromide) salt of alkaline metal; RB and an iodide (or nitrite, or thiocyanate, or selenocyanate, or bromide) salt of alkaline metal.

The following examples illustrate empirical proof of operational advantages of a method of the invention acquired in but several, non-limiting experiments.

Example 1: Formation of MCPPS from Methylene Blue and Salt of Alkaline Metal While the following discussion below is presented in specific reference to KI and methylene blue (MB), it is understood that similar results are obtained with the use of harmless and intert salts such as iodides, nitrites, thiocyanates, selenocyanates and bromides, to name just a few for potentiation of various other single-components PS.

Methylene blue (MB), a phenothiazinium dye, is probably the most commonly studied antimicrobial PS. Several studies have reported its activity in vitro, and in animal models of infection, and MB has received regulatory approval to mediate photodynamic therapy (PDT) of dental infectious diseases such as periodontitis and caries, and is under clinical investigation for nasal decontamination and chronic sinusitis in some countries. MB is well known to act by both the type 1 mechanism (producing reactive oxygen species including hydroxyl radicals) and by the type 2 mechanism (producing singlet oxygen), although singlet oxygen is more often credited with being the most effective antimicrobial species produced during PDT.

According to the idea of the invention, an MCPPS was created by potentiating the MB-mediated PDI bacteria inactivation with the addition of KI. The increase of efficiency of bacteria inactivation with such MCPPS as compared to the MB alone was empirically demonstrated against $S.$ $aureus$, and $E.$ $coli$ using different concentrations of MB with a constant concentration of KI and also the opposite (using different concentrations of KI with a constant concentration of MB).

Materials.

1) Methylene blue (MB), potassium iodide (KI), Lugol's solution and all other reagents, were purchased from Sigma-Aldrich (St. Louis, Mo.) unless indicated. MB stock solution was prepared in $dH_2O$ and stored at 4° C. in the dark for no more than 24 hrs prior to use. KI solution was prepared in $dH_2O$ as required immediately before experimentation. The singlet oxygen sensor green (SOSG) and hydroxyphenyl fluorescein (HPF) probes to detect singlet oxygen or hydroxyl radicals were purchased from Life Technologies (Grand Island, N.Y., USA).

2) $Staphylococcus$ $aureus$ (NCTC 8325) and $Escherichia$ $coli$ K12 (ATCC 33780) were chosen as representative Gram (+) and Gram (−) bacteria respectively, for in vitro studies. A colony of bacteria was suspended in 25 ml of brain heart infusion (BHI) broth (Becton, Dickinson, and Company, Franklin Lakes, N.J.) and grown overnight in a shaker incubator (New Brunswick Scientific, Edison, N.J.) at 120 rpm in aerobic condition at 37° C. An aliquot of 1 ml from overnight suspension was refreshed in fresh BHI for 2 hours at 37° C. to mid-log phase. Cell concentration was estimated by measuring the optical density (OD) at 600 nm [OD of $0.8 = 10^8$ colony forming units (CFU) cells/mL]. Bacterial suspension was centrifuged, washed and re-suspended in PBS to arrest microbial growth, and used ($10^8$ CFU) for the in vitro or in vivo experiments.

Experiments With MCPPS Containing a Mix of Solutions of the Single-component PS and Inert Salt.

Figure 2A:
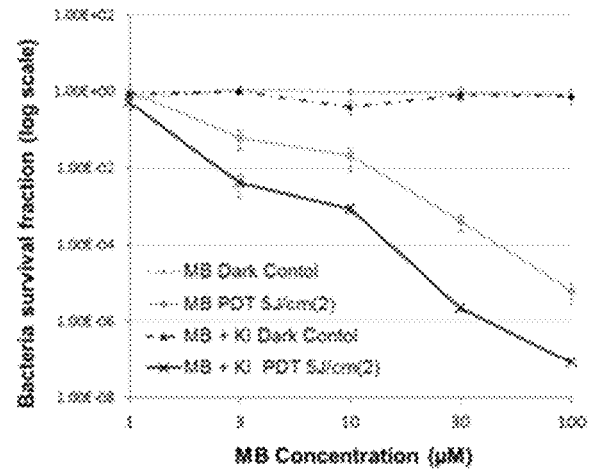
FIGS. 2A, 2B, 2C present plots illustrating results of potentiation of MB-antibacterial PDI by addition of potassium iodide, in vitro, with respect to *E. coli;*

In vitro PDI studies were carried with $S.$ $aureus$ and with $E.$ $coli$. Cells ($10^8$ CFU; 500 μL) were incubated with different concentrations of MB (0-50 μM) for 15 minutes with either addition or not of 10 mM KI. An aliquot of 100 ul was used as dark control from each sample, another (100 ul) was irradiated with 5 J/cm$^2$ dose of light (660 nm light) and then placed in a new 96 well plate. The aliquots were serially diluted 10-fold in PBS to give dilutions of $10^1$ to $10^5$ times in addition to the original concentration. From each dilution 10 microleter aliquots were seeded horizontally on BHI agar. Plates were streaked in triplicate and incubated for 14-18 hours at 37° C. in the dark to allow the growth of colonies. Each experiment was performed at least three times. Results reported in FIGS. 1A and 2A respectively show the survival fraction curves obtained against the Gram (+) bacterium $S.$ $aureus$ and or Gram (−) bacterium $E.$ $coli$, incubated for 20 minutes with a range 0-100 μM of MB for both strains with and without addition of 10 mM KI. The addition of KI produced an increase in bacterial killing of 4 and 2 logs for $S.$ $aureus$ and $E.$ $coli$ respectively.

Figure 1B:
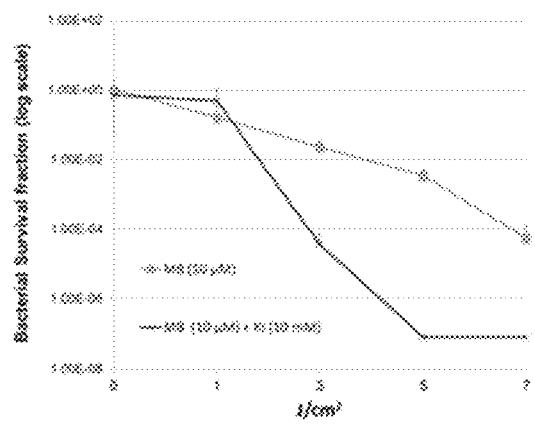
Figure 2B:
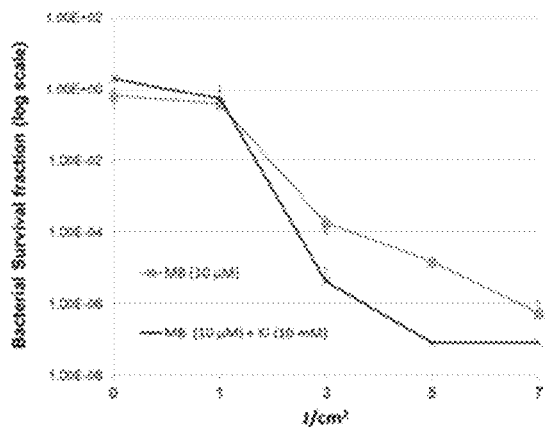

To verify if the bacterial inactivation was also dependent on the light dose, the cells were treated with a single concentration of MB (10 μM) and KI (10 mM) and we irradiated with a range of doses of light (0-7 J/cm$^2$). After treatment, an aliquot from each group of treatment was placed in a new 96-well plate and serial dilution was performed as described above. FIGS. 1B and 2B verify the light-dependent photochemical process in the bacterial killing, by presenting the survival fraction curves obtained against $S.$ $aureus$ and $E.$ $coli$ incubated for 20 minutes with 10 μM MB for both strains with and without 10 mM KI and delivering increasing doses of light (0-7 J/cm$^2$). In these experiments, with addition of KI, an increase in bacterial killing for both strains was observed. The increase in both experiments was more pronounced in $S.$ $aureus$ than $E.$ $coli$.

Figure 1C:
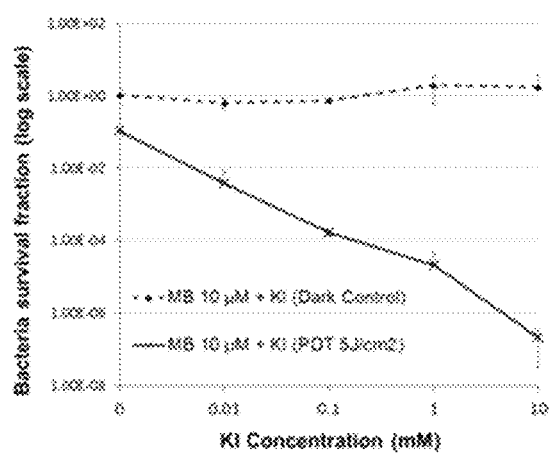
Figure 2C:
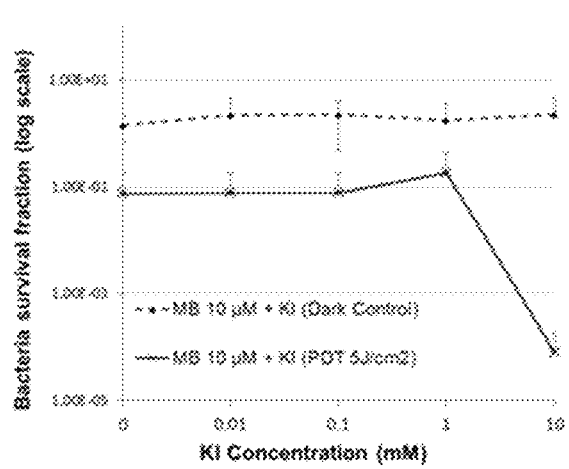

Finally, to investigate the dependency of bacteria inactivation by KI concentration the same experiment were performed using 10 μM MB and adding KI (in the range of concentrations between 0 and 10 mM) just before irradiating the so-treated bacteria with 5 J/cm$^2$ of red light at the wavelengths in the red portion of the optical spectrum (such as 660 nm, for example). FIGS. 1C and 2C present results demonstrating a dose-dependent increase of bacteria killing in $S.$ $aureus$ starting from 0.01 mM KI while the enhancement of $E.$ $coli$ killing is only observed with 5 mM KI.

A key parameter in PDI was also investigated. The binding of PS to the cell membrane or the uptake of PS into the cells obtained during incubation with MB is a critical point in PDI. For this reason we verified the bacteria killing in presence or not of KI with and without washing the cells with PBS after MB incubation and before adding KI to $S.$ $aureus$ and $E.$ $coli$ (data not shown). Cells were then either exposed (light) or not (dark) to a range of light doses 0-5 J/cm$^2$ at an irradiance of 100 mW/cm$^2$. For the dark control (DC) we incorporated the time of light exposure. Cells were then serially diluted and plated to count CFU. Survival fractions showed an enhancement of bacteria killing in presence of KI was observed in both strains without a wash while no killing was observed after washing of the MB solution from the cells. The presence of unbound MB in the solution is therefore critical in our experimental conditions. The lack of killing without light in all experimental conditions showed that neither the MB alone nor MB plus KI displayed any appreciable dark toxicity. On the basis of these results we concluded that the presence of KI could increase bacteria killing depending on the doses of MB, light and KI concentration. Moreover the binding of MB to the cell membrane is not involved in the increase in bacterial inactivation.

Figure 3A:
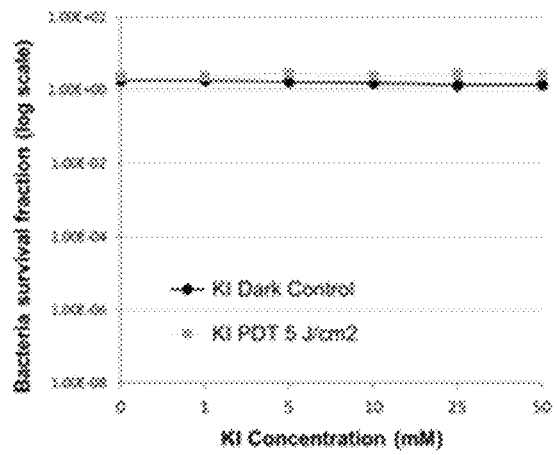
FIGS. 3A, 3B, 3C are plots illustrating effect of potassium iodide alone on bacteria and mammalian cells in vitro.
Figure 3B:
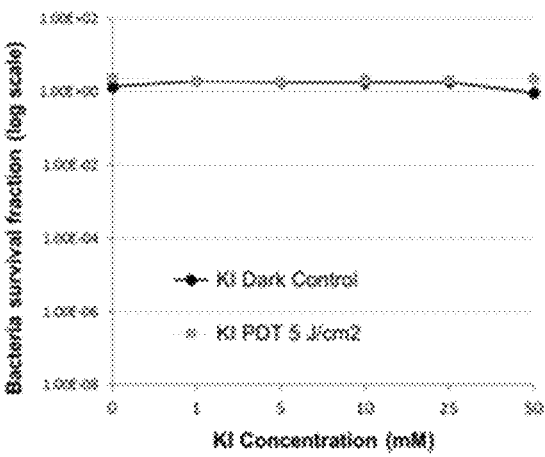
Figure 3C:
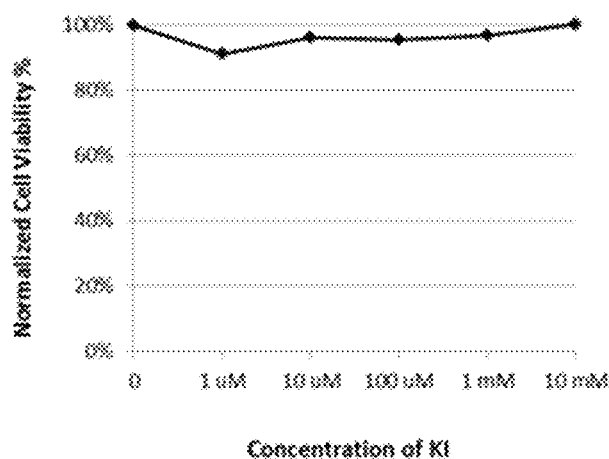

Since there existed a possibility that KI itself could exert an antimicrobial effect, to eliminate or at least account for the direct influence of the KI on the bacteria and to ensure that the final efficiency of the PDI process is attributed to the potentiation of the MB with the KI, additional qualitative performance evaluation tests were performed. Specifically, the bacteria cells ($10^8$ CFU; 500 uL) were incubated with different concentrations of KI (0-50 mM) for 10 minutes in order to verify the toxicity of KI. An aliquot of 100 µl from each sample, was used as dark control, another (100 µl) was irradiated with 5 J/cm$^2$ dose of light (660 nm light) and then placed in a new 96 well plate. The aliquots were serially diluted as before. The results presented in FIGS. 2A, 2B (for S. aureus and E. coli) verified that KI itself was not responsible for the increased potency of the PDI treatment observed in the experiments with the MCPPS. In particular, after 10 minutes incubation no bacteria killing was found both in DC and after shining 5 J/cm$^2$ dose of red light. To ensure that KI does not have any side effect in in vivo experiments, the effect of KI in vitro on mammalian dermal skin fibroblasts was performed as well. As shown in FIG. 3C, KI did not kill mammalian cells exposed for 3 hours to the range of KI concentration (0.001-10 mM).

It is concluded, therefore, that the effect observed in bacteria killing potentiation is due to the synergistic effect of the PDI process performed when the bacteria are treated with the MCPPS combining the MB and KI together.

In practice, therefore, an embodiment of the invention is implemented by, initially, treating living bacteria to form a first amount of treated bacteria via establishing contact between pre-mixed (for example, in the form of pre-mixed solutions) first and second compositions of matter and the living bacteria. Here, the first composition of matter comprises a single-component photosensitizer PS having a first efficiency in mediating said process on its own, and the second composition of matter has no efficiency in mediating said process on its own.

The innovation offered by adding a potentiating salt—for example, KI—to a single-component PS solution stems from the fact that by interaction of the ROS and KI during light exposure, the bacterial killing was improved. One mechanism may turn on generation of biocidal molecular iodine ($I_2$ and/or $I_3^-$) or hypoiodite (HOI). Alternatively reactive iodide radicals (I. or $I_{\cdot 2}^-$) could be formed by interaction of the PS excited state with KI that would increase the damage to bacterial cell wall constituents.

Fluorescence Probe Experiments.

Figure 4A:
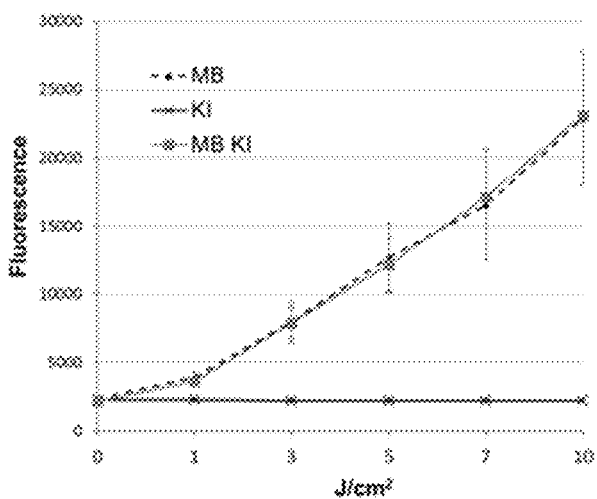
FIGS. 4A, 4B are plots showing the results of fluorescence probe experiments.
Figure 4B:
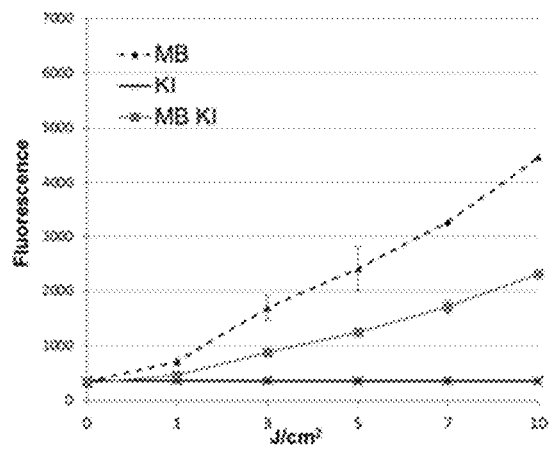

Additional experiments were performed with the use of fluorescent probes—in particular SOSG as a marker of singlet oxygen and HPF as a marker for hydroxyl radical generation—to clarify the mechanisms involved in the effect observed on bacteria killing, we used fluorescent probes. Fluorescent probe experiments were performed in ninety-six-well black-sided plates. Final concentration of 10 µM SOSG or was added to 5 µM MB solution with and without addition of KI in 100 µL PBS per well. Fluorescence spectrometry (SpectraMax M5 plate reader, Molecular Devices, Sunnyvale, Calif.) used excitation and emission at 504 nm and 525 nm for SOSG and 490 nm and 515 nm for HPF, respectively. A range of light doses (0-10 J/cm2) was delivered using red light (660±15 nm band pass filter) at irradiance of 100 mW/cm$^2$ as measured with a power meter (model DMM 199 with 201 standard head; Coherent, Santa Clara, Calif.). The fluorescence was measured after each dose of light was delivered. The presence of KI did not produce any difference in SOSG activation (FIG. 4A) while a quenching phenomenon for HPF was observed (FIG. 4B). The reduction in probe activation observed in our system could possibly be explained by the recently reported KI-related effect of decrease of in vitro generation of ROS produced by polymorphonuclear leucocytes (PMN) (see Miyachi, Y. and Y. Niwa, Br J Dermatol, 1982. 107(2): p. 209-14.)

Iodine Generation.

Figure 5:
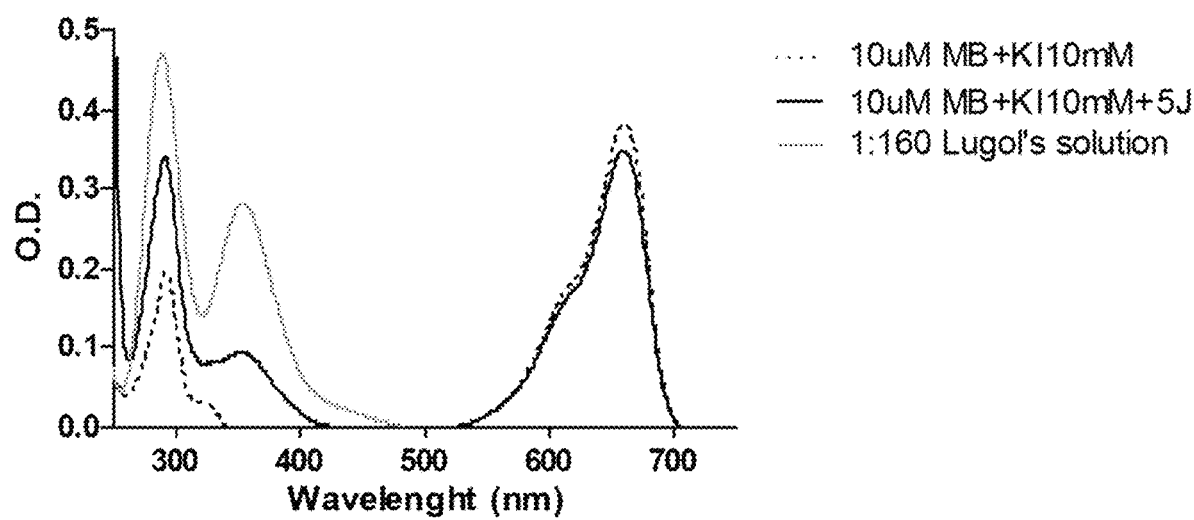
FIG. 5 presents the results of iodine generation experiments.

To verify whether the generation 12 could be responsible for killing the bacteria, the spectra of MB and MB+KI solutions were established before and after shining the light. UV-Vis spectral analysis was carried out using a spectroradiometer (SPR-01; Luzchem Research, Inc., Ottawa, ON, Canada) and showed a peak emission at 365±5 nm. The solutions of MB (10 uM) with and without addition of 10 mM of KI were irradiated with 7 J/cm$^2$ of red light, and afterwards $10^8$ CFU bacterial cells were added to the light-treated solutions in the range of time 0-30 min. CFU were measured as described above. The generation of iodine species was evaluated by measuring the spectral peak at 348 nm. Our positive control was reference 1:160 Lugol's solutions in PBS combined with MB. As shown in FIG. 5, the production of iodine species was observed when light was delivered at 5 J/cm$^2$, and no iodine-representing peak was observed in the spectra before irradiation of the chemical with light.

Potentiating Effect on Bacterial Killing Produced by Addition of Salt of Alkaline Metal to Fenton Reagent or to $H_2O_2$ and HPR.

Figure 6A:
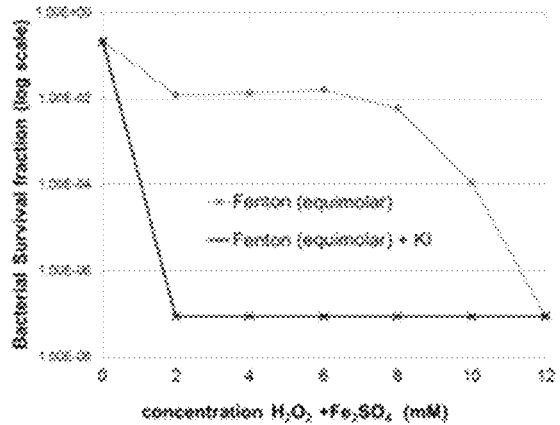
FIGS. 6A, 6B, 6C, 6D are plots illustrating the antimicrobial activity of Fenton reagent (ratio of FeSO4/H2O2 was 1:1) and of a combination (Fenton reagent plus KI) against *S. aureus* (FIGS. 6A, 6C) and against *E. coli*.
Figure 6B:
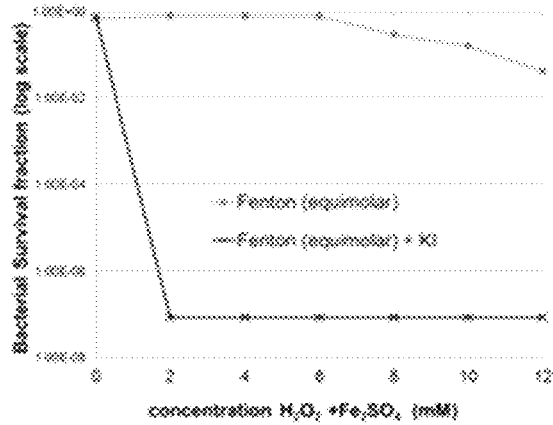
Figure 6C:
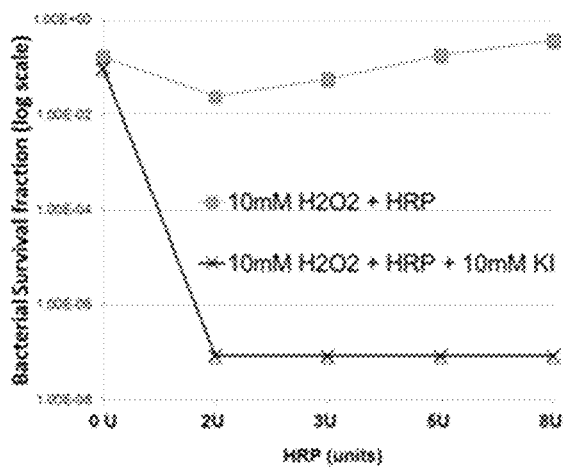
Figure 6D:
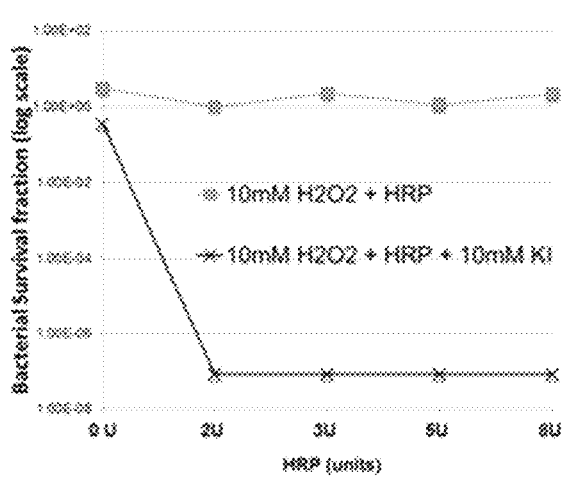

The plots in FIGS. 6A, 6B, 6C, 6D show the antimicrobial activity of Fenton reagent (ratio of FeSO4/H2O2 was 1:1) and of a combination (Fenton reagent plus KI) against S. aureus (FIGS. 6A, 6C) and E. coli. (FIGS. 6B, 6D). During the preparation to the measurement, suspensions of bacteria ($10^8$ CFU/ml) were incubated at room temperature with various concentrations of Fenton reagent (equal concentrations of $H_2O_2$ and $FeSO_4$) or with 10 mM $H_2O_2$+HRP (0-8U) with and without addition of 10 mM KI. In both experiments bacterial cells were incubated with reagents diluted in pH 7.4 PBS for 1 hour. At the end of the incubation time 100 µl aliquots were placed in 96 wells from each tube and serially diluted on agar plates to determine CFU.

When Fenton reagent was combined with 10 mM KI, a dramatic potentiation (up to 6 logs) of the antimicrobial effect of the Fenton reaction as observed, similar to prior reports in related art. This could imply HO. reacted with KI produces iodide radicals from HO., which potentiated bacterial killing in cell suspension. The same dramatic potentiation in bacterial killing (about 6 logs) when we added KI to the reaction $H_2O_2$+horseradish peroxidase (HRP), also substantiating results of similar experiments in related art. The mechanism of action was proposed to be oxidation of iodide anion to iodine radicals by the enzyme-hydrogen peroxide transition state (Kohler, H. and H. Jenzer, Free Radic Biol Med, 1989. 6(3): p. 323-39; as originally worked out by Chance B., Adv Enzymol Relat Areas Mol Biol, 1999. 73: p. 3-23).

Relevance of Long-Lived Reactive Iodine Species ($I_2$ or HOI) to Bacterial Killing.

To verify if long-lived species such as molecular iodine ($I_2$) or hypoiodous acid (HOI) could be responsible for increased bacterial killing we added bacteria after completion of light delivery.

Figure 7A:
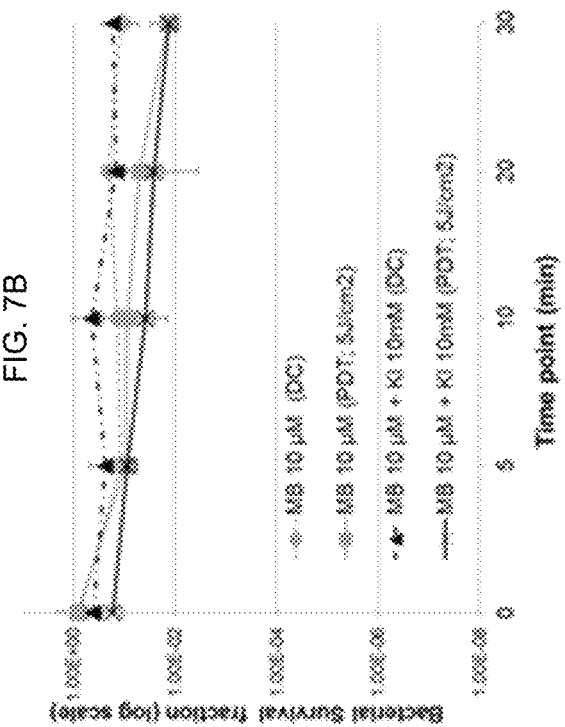
FIGS. 7A, 7B illustrate influence of long-lived reactive iodine species ($I_2$ or HOI) on inactivation of bacteria.
Figure 7B:
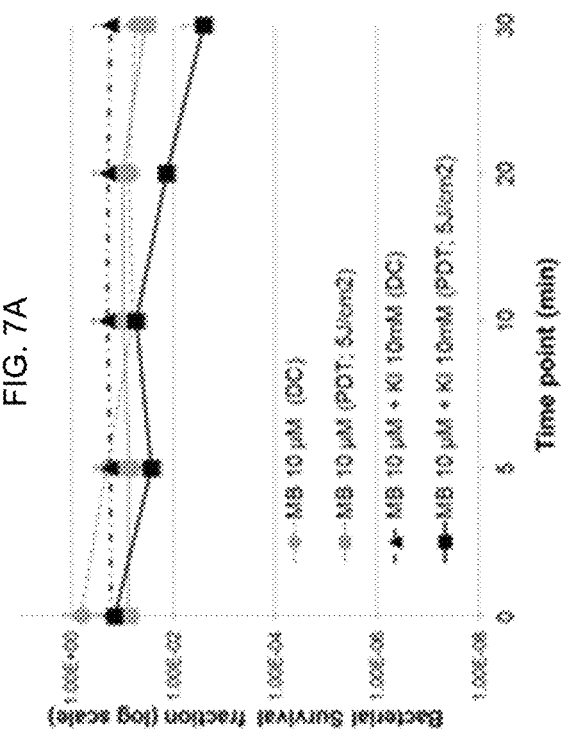

We irradiated with 5 J/cm$^2$ the solutions containing MB or MB+KI to generate the iodine species observed in the spectra described above. Since $I_2$ is a stable molecule, and even HOI is reasonably stable with a measurable half-life, by incubating the cells in a solution that could contain photochemically produced bactericidal concentrations of $I_2$ or HOI, we expected to observe bacterial killing. We added bacterial cells and we evaluated the survival fraction of bacteria in an incubation time range between 5 and 30 minutes. As shown in the plots of FIGS. 7A, 7B we did not observe any bacterial killing in both strains. This demonstrated that even if in our system generated $I_2$ and HOI, there was no evidence that the concentration produced could be responsible for bacterial killing observed in PDI in presence of KI. No killing was observed in dark control.

Example 2: Formation of MCPPS from Fullerene and Salt of Alkaline Metal

In this example, the employ of an MCPPS formed by addition of iodide anion to fullerene material (specifically, a C60 fullerene bisadducts), otherwise singly mediating antimicrobial photodynamic treatment, clearly demonstrated increase of efficacy of the photodynamic treatment as compared with the that utilizing only the fullerene. Studies with members of three different classes of pathogen were carried out to demonstrate the broad-spectrum nature of the approach.

Fullerenes (C60, C70, C84) are a class of closed cage carbon molecules with a large number of conjugated double bonds that efficiently absorb light in the UV and visible spectral regions. The excited singlet state undergoes efficient intersystem crossing giving these molecules a high triplet quantum yield. Pristine fullerenes are highly hydrophobic and insoluble in aqueous media making them largely unsuitable for biological applications. However the fullerene carbon cage can be derivatized by attachment of organic ligands containing suitable functional groups to provide water solubility and to enable the fullerenes to recognize and bind to biological targets such as bacterial cells. One of the most suitable functional groups for both these purposes is the quatemary ammonium group that provides constitutive cationic charges.

The use of fullerenes as single-component PS to mediate a PDI-type treatment may be one of the most promising biomedical applications of nanotechnology. Although their absorption spectrum is mainly in the shorter wavelength regions of the electromagnetic spectrum, which may considered a disadvantage, they have several other properties that make them advantageous. Fullerene molecules have high photostability that makes them resistant to photobleaching that can be the limiting factor in the case of more usual PS derived from tetrapyrrole or phenothiazinium structures. They are particularly effective at mediating Type 1 photochemical mechanisms as opposed to the Type 2 generation of singlet oxygen that dominates other PS.

Irradiation Setup.

UVA light (360+/−20 nm, American Ultraviolet Co, Lebanon, Ind.) was delivered to a spot with diameter 15 cm at an irradiance of 20 mW/cm$^2$. The irradiance was measured using a model IL-1700 research radiometer/photometer (International Light, Inc., Newburyport, Mass.) using a wavelength range of 250-400 nm. White light source at 400~700 nm (Lumacare, Newport Beach, Calif.) was used to deliver light over a spot diameter 3-cm at an irradiance of 100 mW/cm$^2$ as measured with a power meter (model DMM 199 with 201 standard head; Coherent, Santa Clara, Calif.)

Bacterial Strain and Culture Conditions.

Here, the used *A. baumannii* strain had previously been engineered to be bioluminescent using the lux ABCDE plasmid (Dai T. et al., Antimicrob Agents Chemother 2009; 53(9):3929-3934). The used methicillin-resistant *S. aureus* (MRSA) strain was USA300 LAC (Los Angeles County clone), a CA-MRSA strain. The USA300 LAC was chromosomally transduced with the transposon for the bacterial luciferase gene operon lux ABCDE (pAUL-ATn4001 lux-ABCDE Km(r); Caliper Life Sciences, Hopkinton, Mass.) to give USA300 LAC:lux), allowing a real time monitoring of the extent of bacterial infection in living. Both bacterial species were routinely grown in brain heart infusion (BHI) medium supplemented with 50 μg/mL kanamycin in an orbital incubator overnight. The overnight suspension was centrifuged, washed with phosphate buffered saline (PBS), and re-suspended in fresh BHI medium to a cell density of 10(8) cells/mL (measured by optical density) for experimental use. The bioluminescent *C. albicans* strain used was CEC 749 as described in Enjalbert B. et al. Infect Immun 2009; 77(11):4847-4858. The luciferase reporter was constructed by fusing a synthetic, codon-optimized version of the Gaussiaprinceps luciferase gene to *C. albicans* PGA59, which encodes a glycosylphosphatidylinositol-linked cell wall protein. Luciferase expressed from this PGA59-gLUC fusion was localized at the *C. albicans* cell surface allowing the detection of luciferase in intact cells after the addition of the luciferase substrate, coelenterazine. *C. albicans* was routinely grown at 30° C. on yeast peptone dextrose (YPD) agar and sub-cultured in YPD medium to an optical density of 0.65 at 570 nm, which corresponds to $10^7$ colony forming units (CFU)/mL. This suspension was then centrifuged, washed with phosphate-buffered saline (PBS), and re-suspended in PBS at the same cell density for experimental use.

Iodide-Driven Potentiation of PDI Mediated with Fullerenes.

Three mL of *A. baumannii* or MRSA suspension both at ≈10(8) CFU/mL, or 3 mL of *C. albicans* at ≈10(7) CFU/mL in PBS were incubated with LC16 at a concentration of 20 uM for 20 minutes. After the incubation time was complete 30 uL of 1M solution of potassium iodide (or PBS as a control) was added to bring the final KI concentration to 10 mM and the suspensions were immediately transferred were into a 35-mm petri dish at room temperature (21° C.). The suspensions were irradiated with the white light Lumacare probe at an irradiance of 100 mW/cm$^2$ or with the UVA lamp at an irradiance of 20 mW/cm$^2$ with the lid of the petri dish removed. During light irradiation, the suspension was gently stirred by a mini-magnetic bar (Fisher Scientific Co., Norcross, Ga.) at 20 rpm. Aliquots of 300_, of the suspension were withdrawn at 0, 5, 10, 15 and 20 min, respectively, when 0, 30, 60, 90 and 120 J/cm$^2$ white light or at 0, 4, 8, 12 and 16 min, when 0, 5, 10, 15 and 20 J/cm$^2$ UVA light had been delivered. Light controls received light+KI but no LC15. CFU were then determined by serial dilution on BHI agar (YPD agar for *Candida*) plates by the method of Jett B. D. et al. (Biotechniques 1997; 23(4):648-650). Colonies were allowed to grow for 18-24 h at 37° C. for bacteria and at 30° C. for *Candida*. The in vitro experiments were performed in triplicate.

Figure 8A:
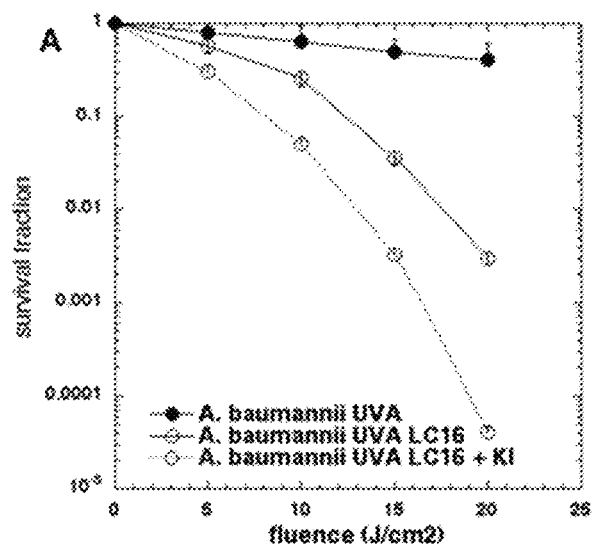
FIGS. 8A, 8B are plots illustrating bacteria inactivation with the use of MCPPS formed by the addition of a salt of alkaline metal to the fullerene (used as a single-component PS) in in vitro antibacterial PDI in *A. baumannii;*
Figure 8B:
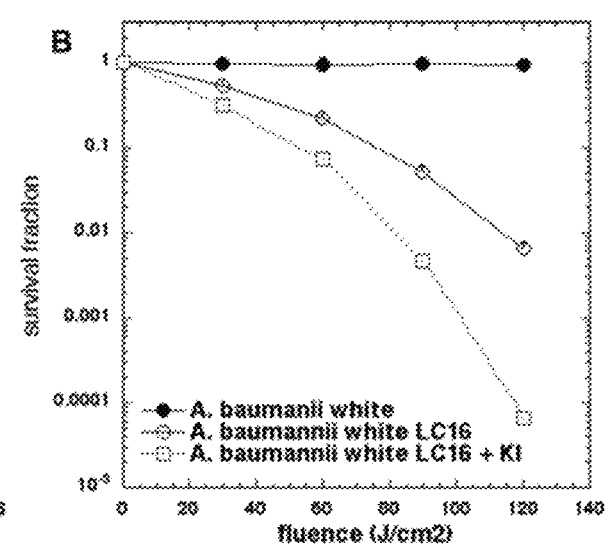

Initially, the use of an MCPPS containing fullerenes and KI for in vitro antibacterial PDI in *A. baumannii* was considered. The curves representing the results are shown for LC16 and LC16 combined with KI, in FIGS. 8(A,B). The fullerenes were excited with white light and with UVA light as there was some evidence that the photochemical mechanism that followed upon fullerene illumination depended on the excitation wavelength. We delivered increasing fluences of light after incubating the bacteria with a constant concentration of 20 µM fullerene with or without the addition of 10 mM KI. The ratio of fluences of UVA or white light employed was roughly in line with the relative absorption coefficients in the spectrum of LC16. This meant that we delivered up to 20 J/cm$^2$ of UVA light, and up to 120 J/cm2 of white light, or six-fold more. Although it is not possible to precisely measure the number of photons absorbed from each light source because of the wide band-widths employed, it is estimated that a 6-fold difference in fluence has occurred. When LC16 was excited by UVA light (FIG. 8A), 1.5 logs of A. baumanii at 15 J/cm$^2$ and 2.5 logs at 20 J/cm$^2$ were deactivated. UVA light alone (no fullerene) deactivated less than 1 log even at 20 J/cm2. When 10 mM KI was added to the incubation mixture to form the MCPPS, the bacterial killing was significantly potentiated (up to 2.5 logs at 15 J/cm$^2$, $p<0.001$, and 4.5 logs at 20 J/cm$^2$, $p<0.001$). The data with white light excitation are shown in FIG. 2B. There was no significant bacterial killing with white light atones as expected. LC16 at 20 uM excited with white light killed 1.5 logs at 90 J/cm$^2$ and 1.5 logs at 120 J/cm$^2$. The addition of 10 mM KI significantly potentiated the killing with 2.5 logs at 90 J/cm$^2$ ($p<0.001$) and 4 logs at 120 J/cm$^2$ ($p<0.001$). The degree of potentiation by KI appeared to be very similar regardless of whether UVA light or white light was used to excite LC16.

Figure 9A:
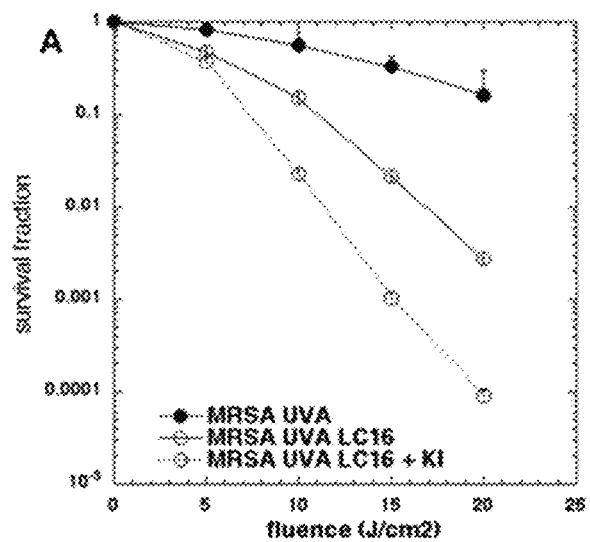
FIGS. 9A, 9B illustrate iodide potentiation of the PDI process in the case of Gram-positive species MRSA.
Figure 9B:
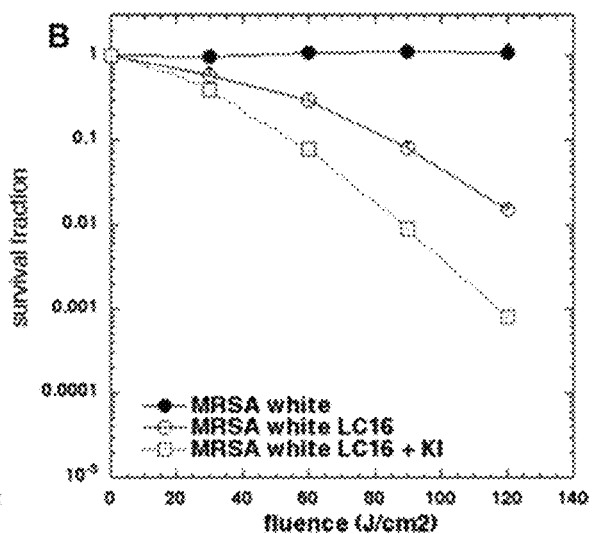

The positive effects of iodide potentiation in the case of Gram-negative A. baumannii, prompted the testing of the Gram-positive species MRSA. The data are shown in FIGS. 9A, 9B. With UVA there was more than 1 log of potentiation with KI (from 1.8 to 3 logs of killing after 15 J/cm$^2$; from 2.7 logs to 4.1 logs after 20 J/cm$^2$). With white light excitation there was again about 1 log of potentiation with KI at 90 and 120 J/cm$^2$. These increases were all highly significant ($p<0.001$).

Figure 10A:
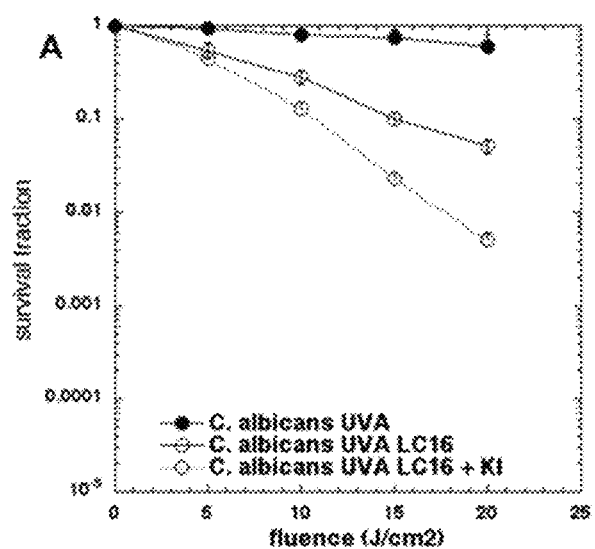
FIGS. 10A, 10B are plots confirming broad-spectrum nature of the enhancement of PDI-process potency due to the use of the MCPPS formed by the combination of the fullerenes and a salt of alkaline metal.
Figure 10B:
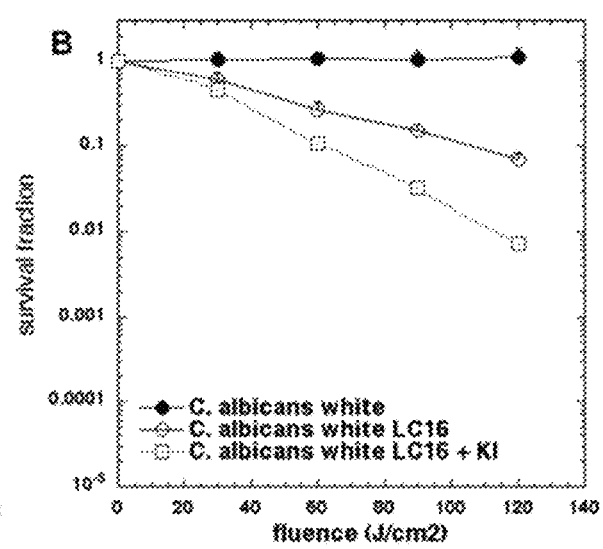

Finally to confirm the broad-spectrum nature of this enhancement of PDI potency due to the use of the MCPPS formed by the combination of the fullerenes and KI, the fungal yeast C. albicans was tested. Although the overall killing of C. albicans by fullerene mediated PDI was lower than that found for the bacterial species, we nevertheless were able to demonstrate a significant ($p<0.001$) potentiation by addition of KI (almost 1 log more killing) with both UVA light (FIG. 10A) and with white light (FIG. 10B).

The above-discussed experiments prove for the first time that the potency of PDI conducted with the use of a multi-component potentiated fullerene material including the combination of a catonic fullerene having an additional tertiary amine chain s with an inert and non-toxic salt is substantially higher than that conducted with the use of only fullerene material. The mechanism of action of the potentiation of fullerene-mediated PDI by addition of iodide anion is incompletely understood. There potentially could be as many as three separate mechanisms operating. These are: (1) Iodide anion could act as an additional source of electrons thus potentiating the Type 1 electron transfer photochemical mechanism of the photoexcited fullerene generating more bactericidal ROS such as hydroxyl radicals; (2) Iodide anion could undergo a one-electron oxidation by the electron transfer to the photoexcited fullerene to form iodide radicals and fullerene radical anions which are expected to be bactericidal; (3) Iodide anion could be oxidized either by Type 1 or by Type 2 photochemical mechanisms to form molecular iodine which is known to be bactericidal. Further studies are actively under way in our laboratory to tease apart the relative contributions of each of these mechanisms to the iodide potentiation of the microbicidal effect.

Notably, the potentiating effect of iodide was observed to about the same extent in the three different classes of microbial cells. The decacationic fullerene was designed to bind and penetrate different classes of microbial cells. It is known that Gram-positive bacteria have permeable cell walls, while fungal cells have a less permeable cell wall structure and Gram-negative bacteria have an impermeable cell wall. However the permeability barrier of Gram-negative bacteria can be overcome by polycationic molecules that disturb the lipopolysaccharide structure by displacing the divalent cations $Ca^{2+}$ and $Mg^{2+}$. The permeability of microbial cells to iodide anion has not been much studied. Although mammalian cells accumulate iodide via the sodium/iodide symporter (highly expressed in the thyroid), only a few rare marine bacterial species have been found to accumulate iodide. At present we believe that the chief site of action of iodide is extracellular, but this remains to be experimentally proved.

One of the chief attractions of an inert salt (such as potassium or sodium iodide, or $KNO_2$, $NaNO_2$, or other salts listed in Table 1) as an adjuvant to potentiate the antimicrobial effect of fullerene-mediated PDI is the lack of toxicity of both the chosen salt and fullerene. (Sherer T. T. et al., J Toxicol Environ Health 1991; 32(1):89-101; Henry T. B. et al. Curr Opin Biotechnol 2011; 22(4):533-537).

Example 3: Potentiation of Antimicrobial Effects of Titanium Dioxide Photocathalysis with Intert Salt of Alkaline Metal Ultraviolet A excitation of titanium dioxide nanoparticles (a wide-band gap semiconductor) in a process called photocatalysis, produces reactive oxygen species that can destroy many classes of microorganisms. As disclosed below, it was demonstrated for the first time that the addition of the non-toxic inorganic salt (such as, in one example, potassium iodide) to $TiO_2$ (referred to as titania) excited by UVA, potentiates antimicrobial photocatalysis in that it potentiates the killing of Gram-positive, Gram-negative bacteria and fungi by up to 6 logs.

The extent of microbial killing depended on the concentration of TiO2, the delivered fluence of UVA light, and critically on the concentration of added KI. Under the conditions we employed that microbial killing obtained by using TiO2 and UVA light alone was minimal, less than 1 log even with 5 mM TiO2 and 20 J/cm2 of UVA. However when iodide was added at 10 mM there was 5 logs of killing with E. coli, and with 100 mM iodide there was eradication (>6 logs killing) with only 5 J/cm2.

Chemicals and Materials.

All chemicals were used as received without any further purification. TiO2 P25 anatase, potassium iodide (KI), Lugol's solution, and all other reagents were purchased from Sigma-Aldrich (St. Louis, Mo.) unless otherwise indicated. Brain-heart infusion (BHI) and yeast peptone dextrose (YPD), Singlet oxygen green sensor (SOSG) for singlet oxygen detection and hydroxyphenyl fluorescein (HPF) for hydroxyl radical were purchased for were purchased from Fisher Scientific. 0.5% starch solution was purchased from Ricca chemical company (Arlington, Tex.). TiO2 stock solution was prepared in distilled $H_2O$ (dH2O) and stored at 4° C. in the dark for no more than 24 h prior to use. KI solution was prepared in dH2O as required immediately before experiments. All the PCD experiments were carried out using 24-well plate under magnetic stirring except ROS probe experiments.

Microbial Strains and Culture Conditions.

The following microbial strains were used in the experiment: methicillin-resistant *Staphylococcus aureus* (MRSA US-300), *Escherichia coli* (*E. coli*) K12, and *Candida albicans* (CEC 749) [PMID 19687206]. Planktonic MRSA, *E. coli* and *C. albicans* were cultured in BHI broth in Erlenmeyer flask overnight in incubator-shaker with speed of 150 rpm. An aliquot of 1 ml from an overnight suspension was refreshed in fresh BHI (MRSA and *E. coli*) for 2 hours at 37° C. or YPD (*C. albicans*) for 4 h at 30° C. to reach mid-log phase. Cell numbers of MRSA and *E. coli* were estimated by measuring the optical density (OD) at 600 nm (OD of 0.6=10^8 cells/ml). Cell number of *C. albicans* was assessed with a hematocytometer. The microbial cells suspension was centrifuged, washed, and resuspended in pH7.4 phosphate buffer (PB) to arrest microbial growth and used (10^8 CFU) for the in vitro experiments.

UVA Light Source.

UVA light was delivered using a 360 nm Light-emitting diode (LED) light source (Larson Electronics LLC, Kemp, Tex.). Emission spectrum measurement of this lamp by a spectroradiometer (SPR-01; Luzchem Research Inc. Ottawa, ON, Canada) showed a peak emission at 360±5 nm. By manipulating the distance between the UVA LED and the target to be irradiated, the irradiance was. The irradiance was 16 mW/cm$^2$, measured using a model IL-1700 research radiometer/photometer (International Light Inc., Newburyport, Mass.) over the wavelength range of 250-400 nm.

Potentiation of TiO2 Photocatalytic Disinfection by Addition of Potassium Iodide In Vitro.

Figure 11A:
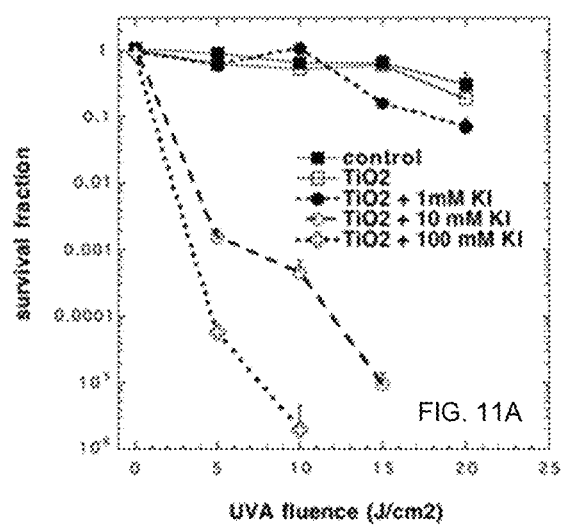
FIGS. 11A, 11B, 11C, 11D, 11E are plots showing the results of potentiation of antimicrobial $TiO_2$ photocatalysis of microbial cells with addition of inert salt of an alkaline metal.
Figure 11B:
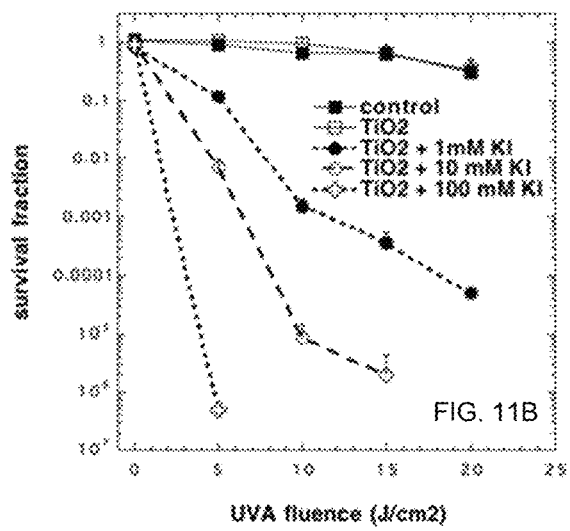
Figure 11C:
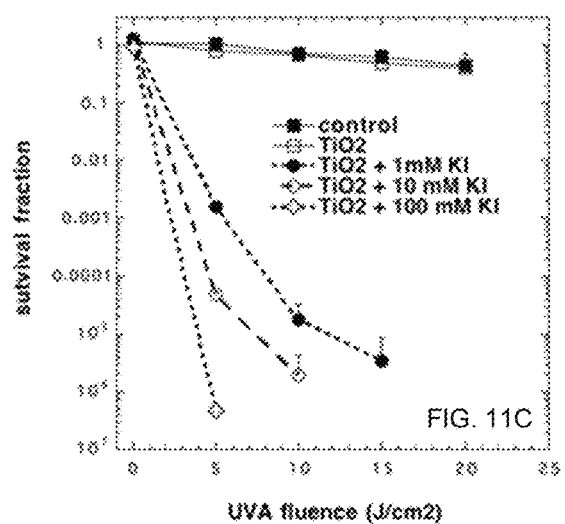
Figure 11D:
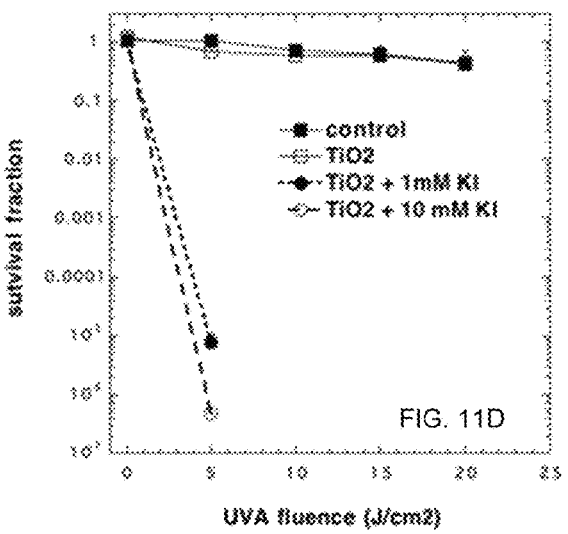
Figure 11E:
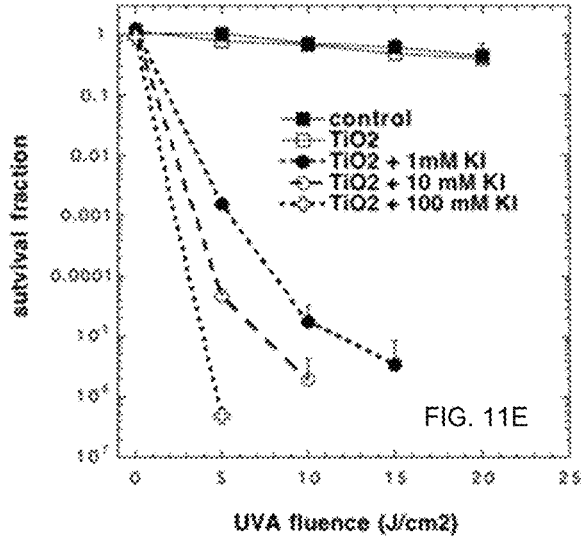

When MRSA cells (10(8) CFU/mL; Gram-positive bacteria, grown overnight at 37° C. (30° C. for *C. albicans*) and bacteria were refreshed for 2-4 hours before being collected through centrifugation and suspended in pH7.4 phosphate-buffer) were mixed with various concentrations of the $TiO_2$ (0 mM, 1 mM, 5 mM) in 24-well plate under magnetic stirring at room temperature, and either left in the dark or irradiated with UVA light at room temperature using a UVA LED to deliver 0-20 J/cm$^2$ light, the viability of cells reached only 1 logs of killing at 20 J/cm$^2$. However, there was a light-dose dependent increase when additional KI (0, 1, 10, or 100 mM) was added to the mixture. The antimicrobial effect was potentiated by 3-5 logs of extra killing (FIG. 11A). When the experiment was repeated with *E. coli* (10(8) CFU/mL; Gram-negative bacteria) there was a light dose-dependent killing, with $TiO_2$ and UVA light alone giving over 6 logs of killing at 20 J/cm$^2$. However when 10 mM KI was added, there was an extra 1-3 logs of bacterial killing on top of that seen with photocatalysis alone (FIG. 11B). When the experiment was repeated with 10(7) CFU/mL of *C. albicans* (fungal yeast) we found similar results. With $TiO_2$ and UVA light alone there was up to 2 logs of killing, but this was increased by 3-5 logs of additional killing by the addition of different concentrations of KI (1-100 mM) to the mixture. Initial conditions of experiments were as follows: FIG. 11A: $TiO_2$ 1 mM on MRSA (10(8) cells/mL); FIG. 11B: $TiO_2$ 5 mM on MRSA (10(8) cells/mL); FIG. 11C: $TiO_2$ 1 mM on *E. coli* (10(8) cells/mL); FIG. 11D: $TiO_2$ 5 mM on *E. coli* (10(8) cells/mL); FIG. 11E: $TiO_2$ 5 mM on *C. albicans* (10(7) cells/mL).

Bacteria Inactivation after Irradiation with Light is Over.

Figure 12:
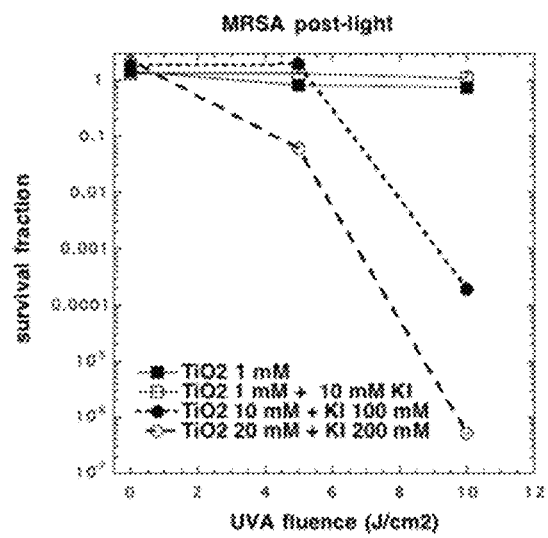
FIG. 12 illustrates deactivation of bacteria added to photoactivated $TiO_2$ after the irradiation was over. $TiO_2$ (1, 10, and 20 mM) was stirred with KI (0, 100 or 200 mM) under UVA light (10 J/cm$^2$) on MRSA (A) cells (10(8) cells/mL) were then added at 5 minutes after the end of the illumination and incubated for 1 hour. Values are means of 3 repetitions and bars are SD.

To investigate how much of the synergistic killing was due to production of a relatively long-lived stable antimicrobial species, the microbial cells were at different times after completion of light delivery. FIG. 12 shows that when MRSA cells were added 5 minutes after the light-treatment to a suspension of TiO2 that had been treated with 10 J/cm$^2$ of UVA light in the presence of 10 and 100 mM iodide there was about 3 and 6 logs of killing, but no killing at all without iodide and with low concentration (10 mM) of iodide. When the bacteria were added to the irradiated suspension 30 min after the end of the illumination period there was the same degree of killing, the killing effect could last for more than 48 hours (data nor shown).

ROS Fluorescence Probes.

In order to gain some information on whether a specific reactive oxygen species produced by the illuminated $TiO_2$ was responsible for oxidizing the iodide, we used two fluorescence probes for ROS that we had previously used in photodynamic therapy studies discussed above to determine whether their activation would be quenched by addition of iodide. ROS probe experiments were performed in 96-well clear-bottom-black plates without magnetic stirring. A final concentration of 5 µM SOSG or HPF was added to 1 mM TiO2 suspension with or without the addition of 100 mM KI in 100 µl PB per well. Probe was illuminated with UVA light ($TiO_2$ (0, 0.1 or 1 mM) was illuminated with UVA light (0-7.5 J/cm2) in the presence of KI (10 mM). Fluorescence was measured in plate reader after each does of light had been delivered of light. The fluorescence intensity was determined using a fluorescent plate reader (SpectraMax M5 plate reader; Molecular Devices, Sunnyvale, Calif.) set at ex/em=504/525 nm for SOSG and ex/em=490/525 nm for HPF, respectively. A range of light doses (0 to 7 J/cm2) was delivered using UVA LED (360±5 nm) at an irradiance of 16 mW/cm$^2$ as measured).

Figure 13A:
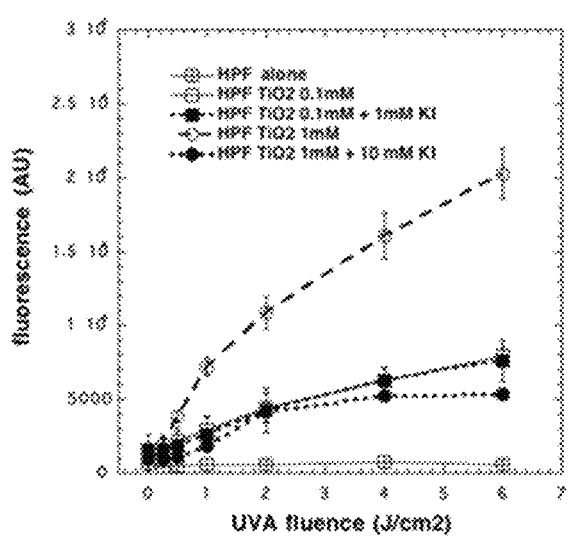
FIGS. 13A, 13B illustrate activation of ROS-specific fluorescence probes by photoactivated $TiO_2$.
Figure 13B:
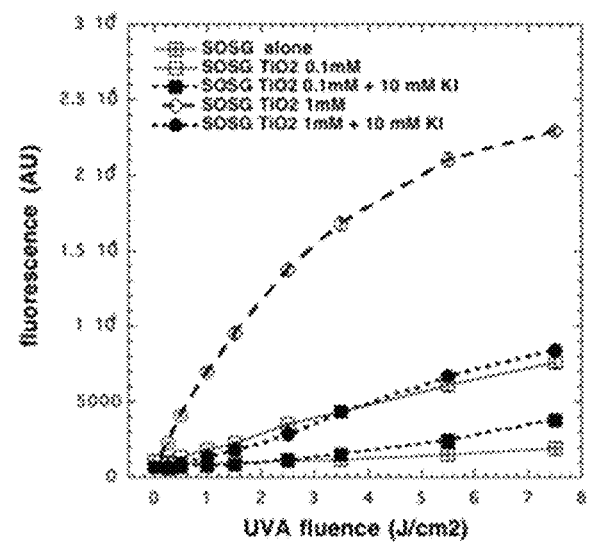

SOSG is relatively specific for singlet oxygen and HPF is relatively specific for detecting hydroxyl radicals. FIG. 13A shows that there was modest but significant quenching of light-activated SOSG fluorescence by addition of 10 mM bromide. FIG. 13B shows that in contrast there was also significant quenching of the photoactivation of the HPF probe.

Iodine Generation.

Figure 14B:
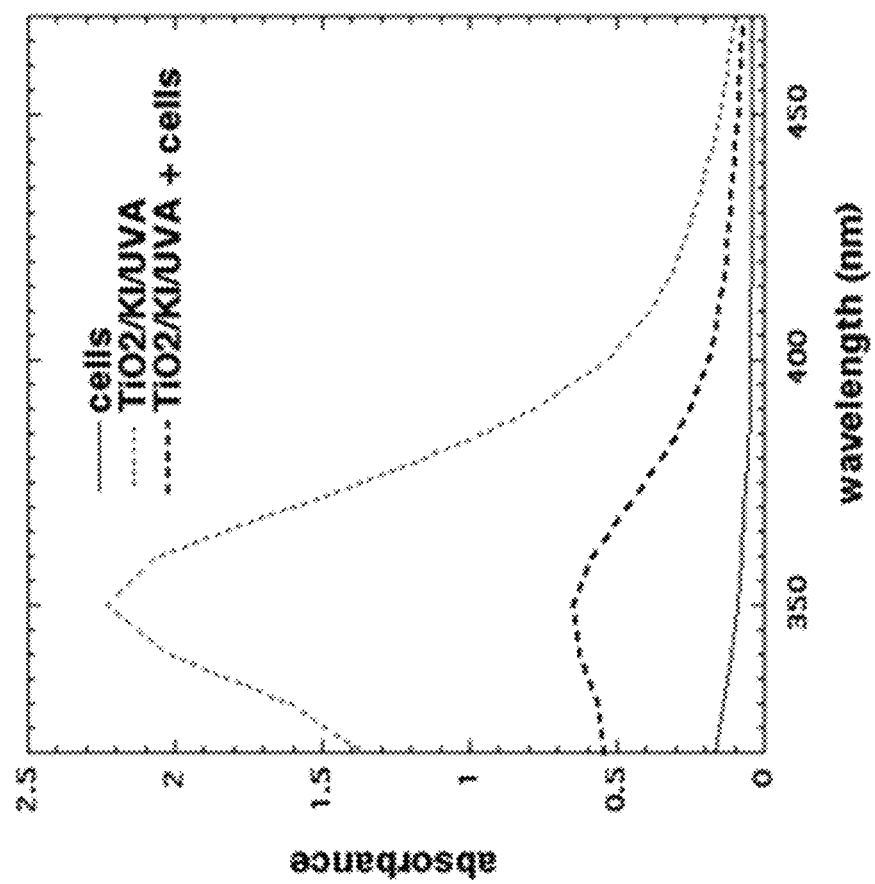
FIGS. 14A, 14B illustrate $I_2$ generation during and post-TiO2 photocatalysis in the presence of KI. Suspension of $TiO_2$ (10 mM) in the presence of KI (100 mM) were stirred with or without bacteria cells (10(8)cells/mL) while being exposed to increasing fluences of UVA light. Supernatant were collected after 5 minutes centrifuge (4000 rpm). Absorbance of $I_2$ was measured using UV-VIS spectrometer.
Figure 14A:
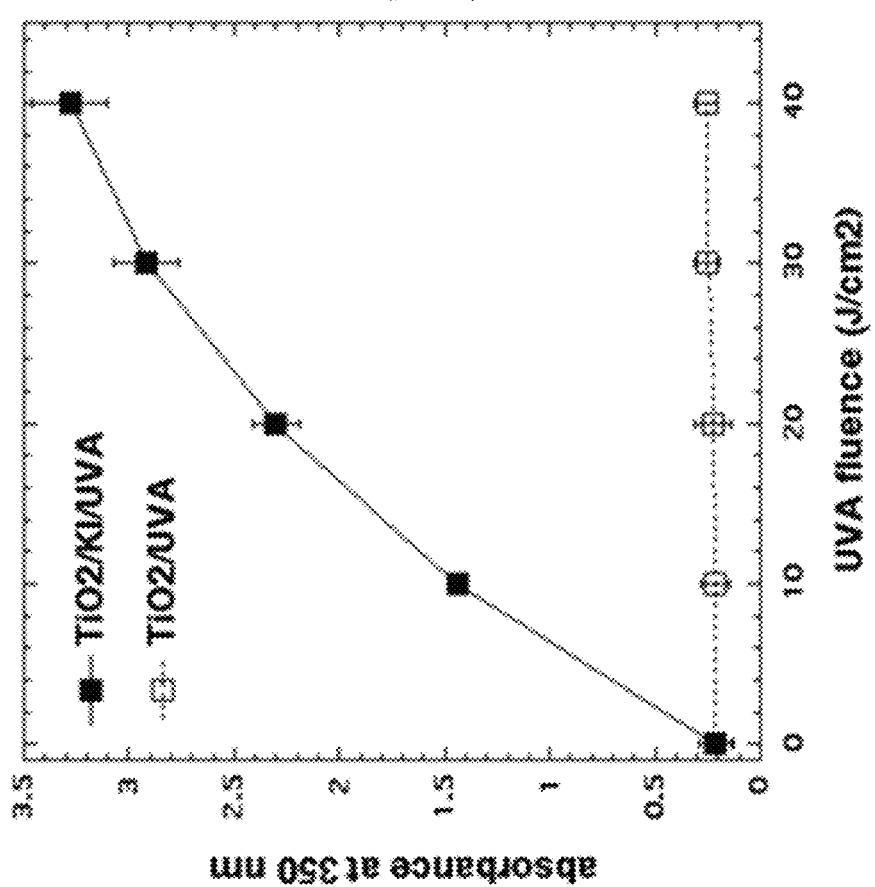

In reference to FIGS. 14A, 14B, I2 generation in a solution containing 1 mM TiO2 and 100 mM KI was detected using UV-visible spectrometer. The spectrum of $TiO_2$/KI suspension was centrifuged at 3500 rpm for 5 mins after shining 0-40 J/cm2 of UVA light. As a reference, spectra were obtained from a 1:200 dilution of Lugol's solution in PB. The UV-Vis absorbance showed a significant increase of I2 at light-dose dependent when shining UVA light 0-40 J/cm$^2$.

It is appreciated that this embodiment of the invention addresses a solution to a long-standing problem of bacterial colonization of medical devices in conjunction with device-surface modification technologies (such as that employing a formation of a thin layer of $TiO_2$ on a surface of a biomedical device to exploit self-disinfecting activity of $TiO_2$). In practice, a surface of a biomedical device such as a dental tool, for example, covered with titania is additionally treated with a salt of alkaline material (or another potentiating component listed in Table 1) prior to triggering the PDI process with irradiating light, to increase a degree of such disinfecting activity by at least one order of magnitude, preferably two orders of magnitude, more preferably three orders of magnitude, even more preferably four orders of magnitude and to reduce the survival fraction of bacteria on such surface by a corresponding factor.

Example 4: Potentiation of Light-Activated PDI Process with Sequential Treatment of Bacteria with Components of MCPPS A colony of UTI89-lux (a persistent uropathogenic Escherichia coli (UPEC) isolate from humans) was inoculated in a 50 ml culture in erlenmyer flask and grow in 37° C. incubator-shaker for 16 hours to stationary phase. Cultures were diluted 1:100 in the M63 media and pipetted (100 µl of each) into each well of 12-well plate with a piece of unbreakable plastic membrane (3 cm*3 cm) in the middle of the well vertically. 3 ml M63 media were added to each well of the 12-well plate for a 37° C. overnight incubation under cover. The plastic membranes were transferred to a new 12-well plate containg fresh M63 media every 24 hours for 5 days. Before the PDI experiments, the plastic membranes growing biofilm were removed and washed with PBS, then vigorously shaken out the liquid over a waste container to remove planktonic cells.

According to the idea of the invention, the biofilm membrane was first incubated in contact with a single-component PS (in this case, a 100 uM Methilene Blue solution in PBS for 30 mins in the dark) and then brought in contact with a potentiating chemical component of one of the MCPPS as discussed above. In this case, specifically, after the incubation the biofilm membrane was washed with PBS twice and inserted in a new 12-well plate with 50 mM or 100 mM KI solution in PBS. 10 J/cm2 660 nm laser light was delivered via a optic filber directly in the solution with irradiance of 30 mW/cm2 to irradiate the biofilm. After PDI experiments, the bacteria cells on biofilm was transferred to 1 ml PBS by scratching with inoculation loop and pipetted into single cells solution. 100 ul aliquot of the biofilm cells solution was serially diluted 10-fold in PBS to give dilutions of 10—1 to 10—5 times in addition to the original concentration, and 10 µl aliquots of each of the dilutions were dropped on square BHI agar plates. Colonies were counted and colony forming units (CFU) were calculated according to (# of colonies× dilution factor)/volume plated=CFU/ml. Survival fractions were routinely expressed as ratios of CFU of microbial cells treated with light and a salt of alkaline metal (or the salt of alkaline metal in the absence of light) to CFUs of microbes treated with neither. Each experiment was performed at least three times.

Figure 15:
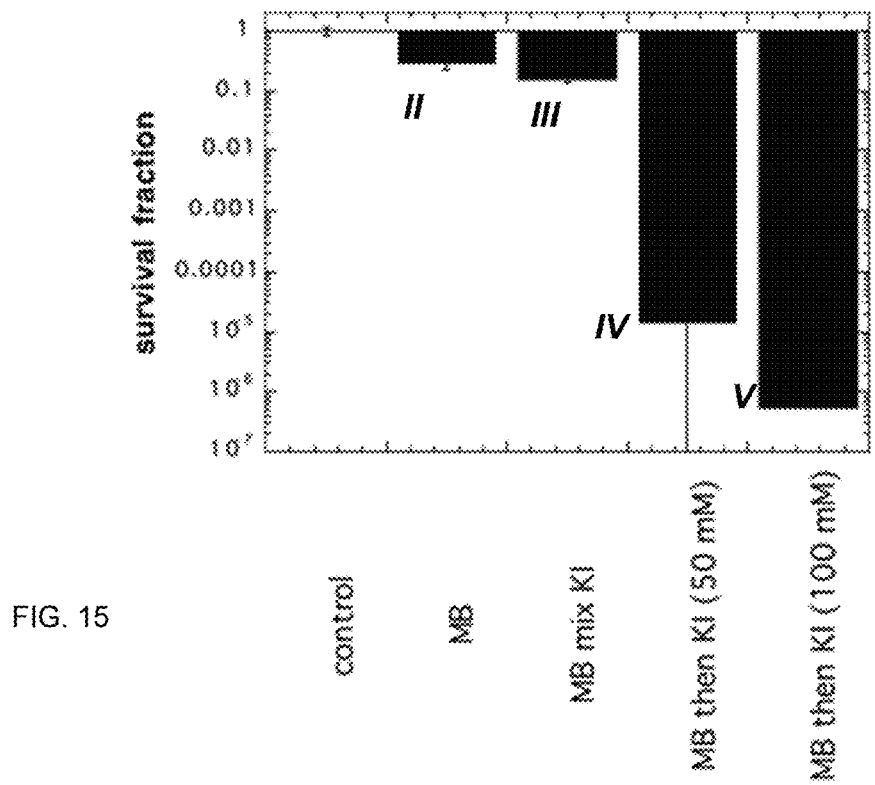
FIG. 15 provides a bar plot illustrating advantages of sequential treatment of bacteria with components of an MCPSS, defined according to the idea of the invention, on increasing the efficiency of the MCPSS-mediated process of PDI.

The results shown as II in FIG. 15 show that the mixture of high concentration of MB and KI killed 2 log of biofilm cells once such mix was applied following the irradiation with light at 660 nm. However, even more potent PDI effect was demonstrated by eradication of biofilm with a two-steps, sequentially performed procedure: incubation of a biofilm with the single-component PA followed by addition of a potentiating chemical composition (such as a salt of alkaline material, for example a 50 mM or 100 mM KI solution, III and IV, respectively) and irradiation with light at a predefined wavelength. Such embodiment of the PDI implemented sequentially according to the idea of the invention reduced the population of the treated bacteria by 4 to 5 or more orders of magnitude as compared to the already improved results (II) achieved due to the potentiation of the MB-mediated PDI with the salt of the alkaline metal. It is appreciated, therefore, that s a result of practical use of one implementation of the method of the invention, when the PDI process is triggered after the target bacteria (which may be located on some surface—for example, a surface associated with a catheter, or another medical tool such as scalpel, or a biological tissue, for example skin) has been sequentially pre-treated (soaked or dampened or otherwise brought into contact) with, a) first, only one component of the pre-determined MCPPS, and then b) another, complementary component of the pre-determined MCPPS, the degree of bacterial inactivation is increased at least 100 times (preferably 1,000 times; more preferably 10,000 times; and even more preferably by 5 orders in magnitude) as compared with the case when pre-treatment of such bacteria is effectuated with the whole MCPPS at once (that is, when all chemical compositions comprising the MCPPS are brought into contact with the bacteria at the same time, for example as a mix).

Example 5: Formation of MCPPS from Rose Bengal and Salt of Alkaline Metal for Potentiation of PDI Rose bengal (RB) is a halogenated xanthene dye already used to mediate antimicrobial PDI in related art. However, while RB is highly active against Gram-positive bacteria, it is largely recognized to be inactive in killing Gram-negative bacteria. This problem has been overcome, as discussed below, by forming the MCPPS from a combination of the nontoxic salt of alkaline metal (in one example—potassium iodide, 100 mM) and RB to potentiate the green light (540-nm)-mediated killing by up to 6 extra logs with the Gram-negative bacteria Escherichia coli and Pseudomonas aeruginosa, the Gram-positive bacterium methicillin-resistant Staphylococcus aureus, and the fungal yeast Candida albicans. The proposed mechanism is postulated to be a singlet oxygen addition to iodide anion to form peroxyiodide, which decomposes into radicals and, finally, forms hydrogen peroxide and molecular iodine. The effects of these different bactericidal species can be teased apart by comparing the levels of killing achieved in three different scenarios: (i) cells, RB, and KI are mixed together and then illumi-nated with green light: (ii) cells and RB are centrifuged, and then KI is added and the mixture is illuminated with green light: and (iii) RB and KI are illuminated with green light, and then cells are added after illumination with the light. We also showed that KI could potentiate RB photodynamic therapy in a mouse model of skin abrasions infected with bioluminescent P. aeruginosa.

Materials and Components.

Rose Bengal was purchased from Sigma-Aldrich (St. Louis, Mo., USA), and an amplex red hydrogen peroxide/peroxidase assay kit was purchased from Invitrogen (Carlsbad, Calif., USA). The singlet oxygen sensor green (SOSG) and hydroxyphenyl fluorescein (HPF) probes used to detect singlet oxygen or hydroxyl radicals were purchased from Life Technologies (Grand Island, N.Y., USA); the starch indicator was purchased from Ricca Chemical Company (Arlington, Tex., USA). RB stock solution (5 mM) was prepared in distilled $H_2O$ ($dH_2O$) and was stored at 4° C. in the dark for no more than 2 weeks prior to use. KI solution was prepared in $dH_2O$ as required immediately before experimentation.

A source of green light was configured from a white lamp and a band-pass filter probe (wavelength, 540±15 nm Lumacare, Newport Beach, Calif., USA) to deliver light over a spot of 4 cm in diameter to simultaneously irradiate four wells of a 24-well plate in vitro or the whole abrasion in vive at an irradiance of 100 $mW/cm^2$. Light power was measured with a power meter (model DMM 199 with a 201 standard head; Coherent, Santa Clara, Calif., USA).

The following microbial strains were used: the Gram-positive bacterium methicillin-resistant Staphylococcus aureus (MRSA) USA 300, Gram-negative bacteria Escherichia coli K-12 (ATCC 33780) and *Pseudomonas aeruginosa* ATCC 19660 (Xen 5P), and strain CEC 749 of the luciferase-expressing fungal yeast *Candida albicans*. A colony of bacteria or fungal yeast was suspended in 20 ml of brain heart infusion (BHI) broth for bacteria or yeast extract-peptone-dextrose (YPD) for *C. albicans* and grown overnight in a shaker incubator (New Brunswick Scientific, Edison, N.J.) at 120 rpm under aerobic conditions at 37° C. for bacteria and at 30° C. for *C. albicans*. For bacteria, an aliquot of 1 ml from an overnight bacterial suspension was refreshed in fresh BHI for 2 to 3 h at 37° C. to mid-log phase. The cell concentration was estimated by measuring the optical density (OD) at 600 nm (OD of $0.6=10^8$ cells/ml). The *C. albicans* cell number was assessed with a hemocytometer and was generally between $10^7$ and $10^8$ cells/ml.

In Vitro Experiments Performed with the RB-Based MCPPS and Evidence of Potentiation of Bacterial Killing Two types of in vitro aPDI experiments were carried out. The first experiments used cells with fixed RB and KI concentrations while varying the dose of irradiating light. The second type of experiments used cells with a fixed RB concentration and a fixed light dose while varying the KI concentration. Here, comparison was performed based on the order of addition of the components and the effect of centrifugation. The initial studies used PDI, with suspensions of bacteria ($10^8$ cells/ml) or *C. albicans* ($10^7$ cells/ml) being irradiated with different fluences of green light (0, 10, and 20 J/cm$^2$) and with different concentration of RB (100 nM for MRSA, 10 μM for *E. coli* and *C. albicans*) with or without 100 mM KI. The aliquots were serially diluted 10-fold in phosphate-buffered saline (PBS) to give dilutions of $10^{-1}$ to $10^{-5}$, in addition to the original concentration, and 10-μl aliquots of each of the dilutions were streaked horizontally on square BHI agar plates for bacteria or YPD agar plates for *Candida*. Plates were streaked in triplicate and incubated for 12 to 18 h at 37° C. (bacteria) or for 24 to 36 h at 30° C. (*Candida*) in the dark to allow colony formation. Each experiment was performed at least three times.

Suspensions of bacteria ($10^8$ cells/ml) or *C. albicans* ($10^7$ cells/ml) were incubated in the dark at room temperature for 30 min with 10 μM RB (for Gram-negative bacteria and *C. albicans*) or 100 nM RB (for MRSA), and then KI at concentrations ranging from 0 to 100 mM in PBS (pH 7.4) was added. Centrifu-gation (5 min, 3,200 rpm) of 1-ml aliquots was used to remove the excess of RB that was not taken up by the microbial cells when experiments required it. The 1-ml aliquots were transferred to a 24-well plate, and the tops of the plates were illuminated with 10 J/cm$^2$ of green light in the dark at room temperature. Care was taken to ensure that the contents of the wells were mixed thoroughly before sampling, as bacteria can settle at the bottom. The aliquots were serially diluted as described above.

When experiments required it, the mixtures of 10 μM RB or 100 nM RB with KI at concentrations ranging from 0 to 100 nM in PBS (pH 7.4) were exposed to green light with fluence of 10 J/cm$^2$, and then bacterial or *C. albicans* cells were added to the so-illuminated mixtures. After 30 min of incubation, the aliquots were serially diluted as described above. Each experiment was performed at least three times.

In related experiments, the mixture(s) of RB (10 μM or 100 nM) and KI at a range of concentrations were exposed to 10 J/cm$^2$ of green light, and then $10^8$ cells/ml of bacteria or $10^7$ cells/ml of *C. albicans* were added and the mixture was incubated in the dark at room temperature for 30 min. The aliquots were serially 10-fold diluted as described above. Each experiment was performed at least three independent times.

Finally, a control group of cells treated with light alone (no RB added) showed the same number of CFU as the absolute control (data not shown). Survival fractions were routinely expressed as ratios of the number of CFU of microbial cells treated with light and RB (or RB in the absence of light) to the number of CFU of microbes treated with neither.

Confocal Scanning Laser Microscopy.

Suspensions of *E. coli* or MRSA ($10^8$ cells/ml) or of *C. albicans* ($10^7$ cells/ml) were incubated in the dark at room temperature for 30 min with 10 μM RB, and then 1-ml aliquots were centrifuged (3 min, 3,200 rpm) to remove the excess of RB. A confocal scanning fluorescence microscope (Olympus American Inc., Melville, N.Y.) was employed to observe the fluorescence emission of RB and cells. Fluorescent images were obtained with a 585-nm band-pass filter. The excitation occurred at 543 nm.

The results of the experiments involving comparison of the microbial kaolin achieved with increasing light doses when KI was added into the mixture of cells incubated with the appropriate concentration of RB, and then irradiated with greenlight, are displayed in FIGS. 23A, 23B, 23C. At the lowest light dose tested (10 J/cm$^2$). RB plus KI and light eradicated (>6 logs of killing) *E. coli*, while only less than 1 log of killing was found when KI was omitted (FIG. 23A). Even with the fluence of 20 J/cm$^2$, the combination of RB and irradiating light resulted in only 2 logs of killing. Methicillin-resistant *Staphylococcus aureus* (MRSA) was killed 1 to 2 logs by the low concentration (100 nM) of RB plus light, while the addition of KI gave 4 logs of additional killing at 10 J/cm$^2$ and eradication at 20 J/cm$^2$ (FIG. 23B). For *C. albicans*, the potentiation was even more dramatic (FIG. 1C). The lowest light dose gave eradication when KI was present, while no killing was found with RB plus light at either fluence.

In order to distinguish between the photochemical oxidation of iodide to give molecular iodine, which is a stable molecule that can exert an antimicrobial effect, and the photochemical creation of reactive iodine species, which would be short-lived and would exert an antimicrobial effect only when the cells were present as the light was delivered, we carried out the following series of experiments. The concentrations of KI were increased, as it became apparent that surprisingly high concentrations were necessary to obtain the maximal potentiation effect. We reasoned that if more killing was observed when the cells were present during the illumination than when the cells were added after the illumination, then it could be deduced that some short-lived species as well as the stable molecular iodine were involved in the killing. In order to study to what extent the RB that was bound to the microbial cells (as opposed to the RB free in solution) was involved in the KI potentiation of aPDI, we also added a step involving the centrifugation of the cells after incubation with RB. The results are shown in FIGS. 24A, 24B, 24C, and 24D. FIGS. 24A and 24B show the results for the Gram-negative species *E. coli* and *Pseudomonas aenrginosa* treated with 10 μM RB and 10 J/cm$^2$ of 540-nm light. The results are quite similar. When all the ingredients were present at the same time (FIGS. 24A and 24B, data shown with closed squares), there was modest killing (1 to 2 logs) at up to 10 mM KI, but at 25 mM KI there was eradication (7 logs of killing). When the cells were added only after the KI and RB had been illuminated, there was no major killing until the KI concentration reached 50 mM (when there was 3 to 4 logs of killing), and at 100 mM KI there was eradication (FIGS. 24A and 24B, data shown with open circles). When the cells that had been incubated with RB were centrifuged, there was virtually no killing even with 100 mM KI. This result is consistent with a lack of binding between RB and Gram-negative bacteria.

FIG. 24C shows the results obtained with the Gram-positive bacterium MRSA. Because MRSA is exceptionally sensitive to RB-mediated aPDI, we used the very low concentration of 100 nM RB. aPDI with a very low concentration of KI (aPDI equivalent to that with RB alone) gave 1 log of killing, and at higher concentrations (up to 25 mM KI) there were 2 logs of killing. However, at 50 and 100 mM KI, there were 5 to 6 logs of killing. When the cells were added after the light, we found only 1 to 2 logs of killing even with 100 mM KI. There was no killing after a spin.

FIG. 24D shows the results obtained with *C. albicans* using 10 μM RB. With all ingredients present (closed squares) and with no KI, we obtained 1.5 logs of killing, and this remained the same until a KI concentration of 10 mM was reached. We began to see potentiation at 25 mM KI, and this increased until eradication was achieved with 100 mM KI. When the cells were added after light (open circles), we saw only minimal killing even at 100 mM KI. When the cells were centrifuged after incubation with RB (FIG. 2D, open squares), we saw about 1 log of killing, and this did not really increase with an increase in the KI concentration up to 100 mM.

Since the results of the experiments where the cells were centrifuged after incuba-tion with RB suggested that only *C. albicans* cells actually bound any RB, we carried out confocal microscopy imaging studies to look at the RB fluorescence in cells that had been centrifuged to confirm these findings. FIGS. 25A, 25B demonstrate that *C. albicans* had a distinct green fluorescence emission around the cells, but the fluorescence did not penetrate to any great extent inside the cells.

Mechanistic Experiments:

A range of experiments was carried out to assess the mechanism of action of the potentiation of RB-mediated aPDI by KI.

(i) Iodine Starch Test.

Mixture(s) of RB (10 μM) and KI (100 mM) were illuminated with green light at increasing fluences, and aliquots (50 μl) were withdrawn after such illumination and added to the starch indicator (50 μl). A microplate reader (absorbance at 610 nm) was used to measure the incremental absorbance after an incremental fluence of 415 nm of light was delivered. Control experiments were performed for (i) RB plus light, (ii) KI plus light, and (iii) PBS alone. Each experiment was performed at least three times.

Initially, it was confirmed that free iodine was generated in a light-dose-dependent manner by using the well-known formation of a blue inclusion complex with soluble starch. See FIG. 26A.

(ii) Amplex Red Assay for Hydrogen Peroxide.

An Amplex red hydrogen peroxide/peroxidase assay kit was used to detect the production of $H_2O_2$ from RB- and KI-mediated PDT. The colorless probe Amplex red (10-acetyl-3,7-dihydroxy-phenoxazine) reacts with $H_2O_2$ in the presence of peroxidase and forms resorufin (7-hydroxy-3H-phenoxazin-3-one). The detection process after (RB+KI)-mediated PDT was done according to the manufacturer's instructions. The reaction systems contained 2 μM RB with added 50 mM KI and were illuminated with increasing fluences of green light, and aliquots were withdrawn and added to 50 μM Amplex red reagent and 0.1 U/ml horseradish peroxidase (HRP) in Krebs-Ringer phosphate (which consists of 145 mM NaCl, 5.7 mM $Na_3PO_4$, 4.86 mM KCl, 0.54 mM $CaCl_2$, 1.22 mM $MgSO_4$, 5.5 mM glucose, pH 7.35). After 30 min of incubation, a fluorescence microplate reader (excitation, at about 530 nm; emission, at about 590 nm) was used to measure the incremental fluorescence after an incremental fluence of green light was delivered. Controls included measurements with the use of (i) RB plus light, (ii) KI plus light, and (iii) Amplex red reagent alone. Each experiment was performed at least three times.

Here, the generation of hydrogen peroxide using the Amplex red assay was confirmed (FIG. 26B), based on the previously reported observation $H_2O_2$ was generated by Photofrin and KI excited by blue light.

We reasoned that there were two possible routes by which hydrogen peroxide could be formed. One involves a one-electron transfer from iodide to singlet oxygen to produce superoxide, which could then undergo dismutation to give $H_2O_2$. The other route involves addition of singlet oxygen to iodide anion to give peroxyiodide, which would decompose to give $H_2O_2$ and iodine.

To distinguish between these two possible routes, we used the nitroblue tetrazolium (NBT) assay for superoxide, reasoning that if we detected superoxide, the first route was suggested, while if we did not detect it, then the second route may take place:

(iii) NBT.

Figure 26C:
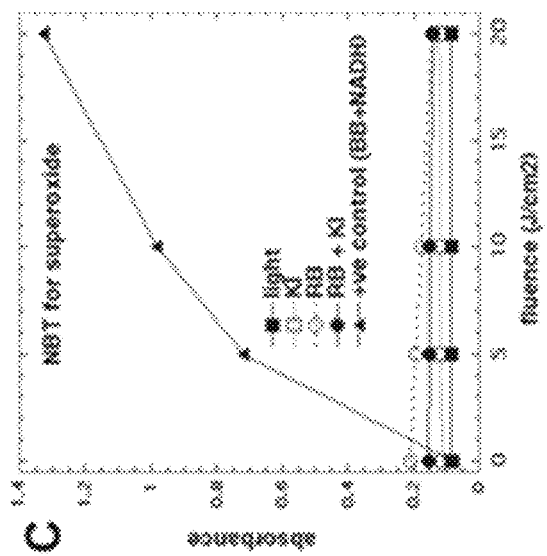
FIGS. 26A, 26B, and 26C: Mechanistic experiments.
Figure 26B:
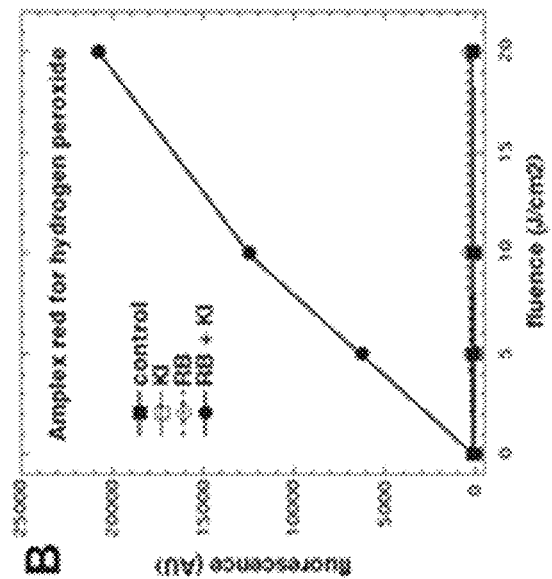
Figure 26A:
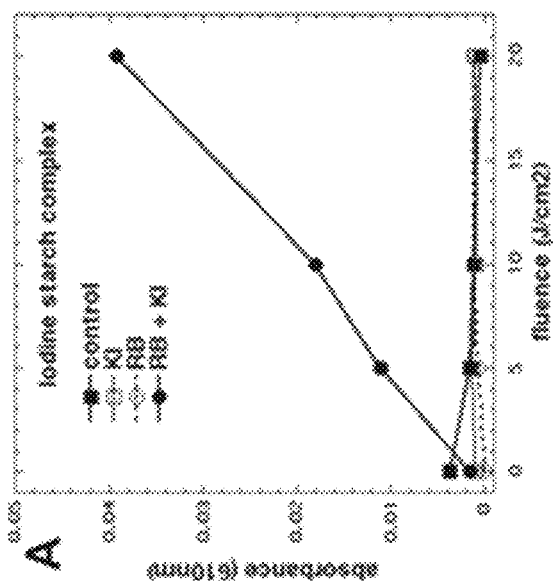

The superoxide assay employed NBT at 20 mM, RB at 10 μM, and KI at 50 mM, and all three were dissolved in PBS. All ingredients were freshly prepared prior to the procedure, an absorbance microplate reader was used to measure the incremental absorbance of the blue product (560 nm) after an incremental fluence of green light was delivered. Controls included (i) RB plus light, (ii) KI plus light, and (iii) PBS alone. Each experiment was performed at least three times. A monocationic fullerene, BB4 (35 μM in combination with 1 mM NADH) (21), excited by 360-nm light was used as a positive control for photogenerated superoxide production. In order to be sure that our failure to detect superoxide was real, we needed a positive control, and this was obtained by illuminating a water-soluble fullerene with UV-A light in the presence of NADH. FIG. 26C shows that there was no detectable superoxide produced by RB plus KI and 540-nm light, while we detected superoxide from the monocationic fullerene BB4 in combination with NADH and 360-nm light.

Further, in order to confirm that singlet oxygen, as opposed to some type I ROS, was the principal mediator of the potentiated microbial killing, we asked whether KI could quench the activation of the fluorescent probe for 102 called "singlet oxygen sensor green" (SOSG) when RB was excited by 540-nm light:

(iv) Activation of SOSG:

Cell-free experiments were performed in 96-well plates. RB was used at 100 nM in PBS, and SOSG (Molecular Probes, Invitrogen, USA) was added to each well at a final concentration of 5.0 μM. KI solution (100 mM KI) was either added or not added. Each experimental group contained four wells. All groups were illuminated simultaneously, and light was delivered in sequential doses of 1.0 to 4 J/cm$^2$. A microplate spectrophotometer (Spectra Max M5; Molecular Devices) was used for the acquisition of fluorescence signals in the slow kinetic mode. The fluorescence excitation was at 505 nm and emission was at 525 nm. Each time after an incremental fluence was delivered, the fluorescence was measured.

Figure 27A:
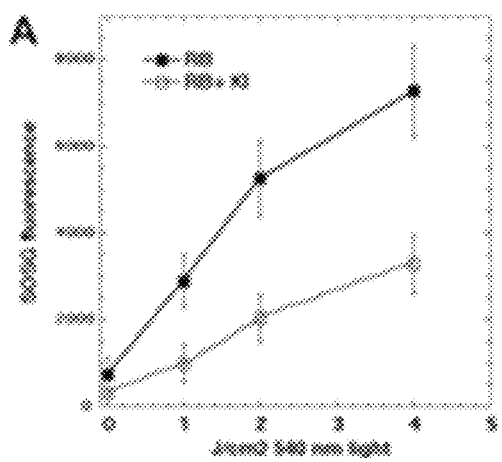
FIGS. 27A, 27B, 27C: Mechanistic experiments.
Figure 27B:
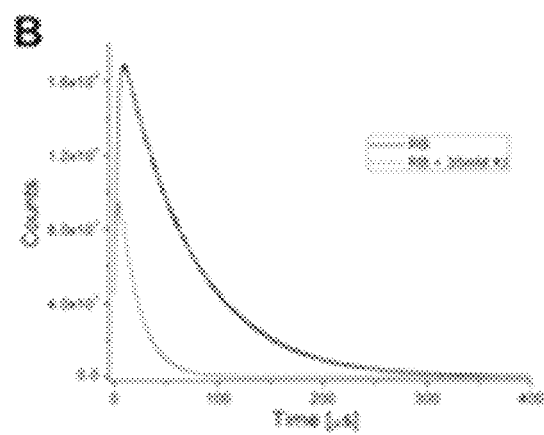

FIG. 27A shows a significant quenching of SOSG activation by addition of 100 mM KI. KI quenching of the singlet oxygen photogenerated by RB was also demonstrated by direct measurement of the singlet oxygen lifetime. FIG. 27B shows representative time-resolved kinetics of the formation and decay of the 1,270-nm phosphorescence detected in a control sample without KI and in the presence of 35 mM KI.

(v) Interaction of Singlet Oxygen with Iodide.

The interaction of iodide with singlet oxygen photogenerated by RB was examined directly by measuring the lifetime of singlet oxygen at different concentrations of KI and indirectly by monitoring the effect of increasing concentrations of iodide on oxygen uptake induced by irradiation of the RB solution with green light. Time-resolved singlet oxygen detection was carried out as follows. Phosphate-buffered (pH 7.2) $D_2O$ solutions of RB (optical density,=0.25 to 0.3 at 550 nm) in a 1-cm-optical-path quartz fluorescence cuvette (catalog number QA-1000; Hellma, Mullheim. Germany) were excited by 550-nm pulses generated by an integrated nanosecond neodymium-doped yttrium aluminum garnet laser system equipped with a narrow-band-width optical parametric oscillator (model NT242-1k-SH/SFG; Ekspla. Vilnius, Lithuania), which delivered pulses at a repetition rate of 1 kHz with energy of up to several hundred microjoules in the visible region. Due to the high efficiency of singlet oxygen photogeneration by RB, the energy of the exciting pulses was attenuated=400 times. The near-infrared luminescence (1,270 nm) was measured perpendicularly to the excitation beam in a photon-counting mode using a thermoelectric cooled near-infrared photomultiplier tube (NIR PMT) module (model H10330-45; Hamamatsu, Japan) equipped with a 1,100-nm-cutoff filter and an additional dichroic narrow-band filter narrow-band pass (NBP), selectable from the spectral range of 1,150 to 1,355 nm (NDC Infrared Engineering Ltd., Maldon, Essex, UK). Data were collected using a computer-mounted peripheral component interconnect (PCI)-board multichannel scaler (model NanoHarp 250; PicoQuant GmbH, Berlin. Germany). Data analysis, including first-order luminescence decay fitted by the Levenberg-Marquardt algorithm, was performed by custom-written software. A typical acquisition time was 20 s. The effect of potassium iodide on the singlet oxygen lifetime was examined over a concentration range of from 0 to 50 mM.

Figure 27C:
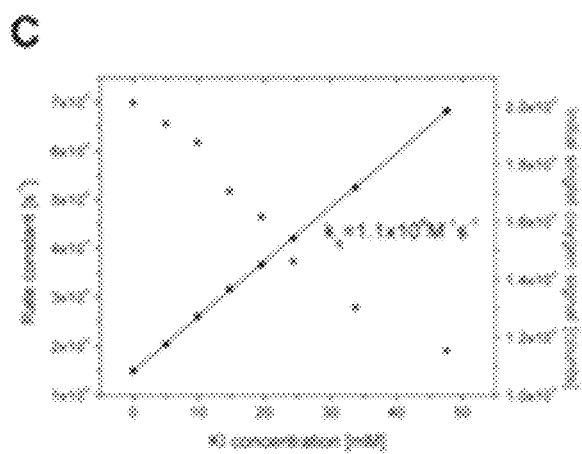

At the concentration used, KI shortened the observable lifetime of the singlet oxygen-dependent luminescence more than 3-fold. It is also apparent that the initial intensity of the singlet oxygen phosphorescence was reduced in the sample containing KI. The observable lifetime of singlet oxygen and its initial intensity as a function of KI concentration are shown in FIG. 27C. The bimolecular rate constant of quenching (kq) of singlet oxygen by KI, derived from the plot, was $1.1*10^6$ l/(m*s). The chemical nature of singlet oxygen quenching by KI is clearly demonstrated by oxygen consumption measurements.

(vi) Oxygen Photoconsumption Measurements.

Time-dependent changes in the oxygen concentration induced by light were determined by electron paramagnetic resonance (EPR) oximetry using 0.1 mM 4-hydro-3-carbamoyl-2,2,5,5-tetramethyl-pyrrolin-1-oxyl (mHCTPO) as a dissolved-oxygen-sensitive spin probe. Samples containing 25 μM RB in PBS, pH 7.2, were irradiated in EPR quartz flat cells in the resonant cavity with 516- to 586-nm (35-mW/$cm^2$) light derived from a 300-W high-pressure compact arc xenon lamp (Cermax; model PE300CE-13FM/Module300W; PerkinElmer Opto-Electronics, GmbH, Wies-baden, Germany) equipped with a water filter, a heat-reflecting mirror, a cutoff filter blocking light below 390 nm, and a green additive dichroic filter (catalog number 585FD62-25; Andover Corporation, Salem, N.C., USA). For EPR, samples were run using microwave power of 1.06 mW, a modulation amplitude of 0.006 mT, a scan width of 0.3 mT, and a scan time of 21 s. Thirty subsequent scans were acquired every 30 s. EPR measurements were carried out using a Bruker EMX-AA EPR spectrometer (Bruker BioSpin, Rheinstetten, Germany).

Figure 27D:
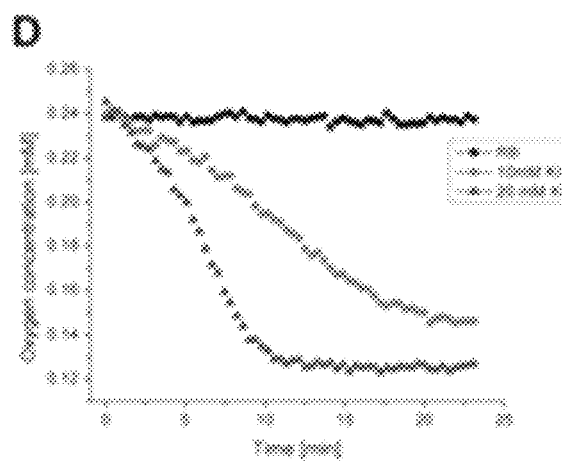
FIG. 27D: oxygen consumption by illuminated RB in the presence and absence of 2 concentrations of KI.

FIG. 27D shows that while in the absence of KI there was no measurable oxygen consumption, addition of KI induced the depletion of oxygen, with the initial rate being dependent on the KI concentration.

In VivoExperiments Performed with the RB-Based MCPPS Included:

(i) Bacterial Strain and Culture Conditions.

The *Pseudomonas aerugenosa* strain used in this work was ATCC 19660 (Xen 5P). Bacteria were routinely grown in BHI with aeration in an orbital incubator at 100 rpm and 37° C. overnight to stationary phase. An aliquot of this suspension was then refreshed in fresh BHI to mid-log phase. Cell numbers were estimated by measuring the OD at 600 nm (OD of 0.6=$10^8$ CFU cells/ml). The bacterial suspension was centrifuged, washed, and resuspended in PBS, and the suspension was diluted 10-fold for the in vivo experiments.

(ii) Bioluminescence Imaging.

An IVIS Lumina series III in vivo imaging system (PerkinElmer, Inc., Waltham, Mass., USA) was applied for bioluminescence imaging on a daily basis until the disappearance of the infection by bioluminescence imaging. Using the photon counting mode, an image can be obtained by detecting and integrating individual photons emitted by the bacterial cells. Prior to PDT and imaging, mice were anesthetized by intraperitoneal (i.p.) injection of a ketamine-xylazine cocktail. Mice were then placed on an adjustable stage in the imaging chamber positioned directly under the camera. A grayscale background image of each mouse was made, and this was followed by the collection of a biolumines-cence image of the same region displayed in a false color scale ranging from red (most intense) to blue (least intense) and superimposed on the grayscale image. The signal from the bioluminescence image was quantified as the region of interest (ROI), with absolute calibrated data being given as the number of photons/(s $cm^2$ sr), using the IVIS software.

(iii) *Pseudomonas aeruginosa* Infection in Mice.

All animal experiments were approved by the Subcommittee on Research Animal Care (IACUC) of the Massachusetts General Hospital and met National Institutes of Health (NIH) guidelines. Adult female BALB/c mice that were 6 to 8 weeks old and that weighed 18 to 21 g were used (Charles River Laboratories, MA, USA). Mice were given access to food and water ad libium and maintained on a 12-h light/12-h dark cycle under a room temperature of 21° C. Mice were anesthetized by i.p. injection of a ketamine-xylazine cocktail. The dorsal skin of the mice was shaved with an electric razor. To create abrasion wounds, surgical scalpels were used to gently scrape the epidermis off an area of approximately 1 $cm^2$. The depth of the wound was no more than the shallow dermis. After creating the wounds, an aliquot of a 50-μl suspension containing $5 \times 10^5$ CFU of *P. aeruginosa* in PBS was inoculated over each defined area containing the abrasion with a pipette tip. Bioluminescence images were taken immediately after the inoculation of bacteria to ensure that the bacterial inoculum applied to each abrasion was consistent.

(iv) In Vivo PDT.

Mice were divided into four groups of 5 mice each. The sample size was determined by an 80% power to distinguish between the PDT with the use of RB from the PDT with the use of the mix of (RB+KI) at a significance level with a P value of 0.05 with a large effect size in relative light unit (RLU) measurements. The groups were as follows. (i) The infected control group consisted of mice whose wounds were only infected with *P. aeruginosa*. (ii) The dark control group consisted of mice treated with RB with KI but no light. (iii) The RB PDT group consisted of mice treated with RB only but irradiated with 540-nm light. (iv) The combination of (RB and KI) PDT group included mice irradiated with 540-nm light in the presence of RB and KI. At 30 min after application of the bacteria to the abrasions, a small aliquot of RB solution (500 µM) alone or RB (500 µM) mixed with KI (1 M) solution was added to the PDT-treated wound and also to the dark controls. Initially, 50 µl of the RB solution was added to the abrasions and incubated for 10 min to bind to and penetrate the bacteria. Then, the wounds were irradiated with green light at a fluence of up to 20 J/cm$^2$, and luminescence imaging was performed after irradiation. In this case, the mice were imaged daily to quantify the recurrence of bioluminescence until the bioluminescence disappeared or the animals were determined to be moribund and euthanized (this did not occur with the strain of *P. aeruginosa* used in the present study).

(v) Histological Analysis.

Two mice per group were used for further histological analysis. The procedure was the same as that described above. The mice were then sacrificed at the first day (24 h) after the experiment to compare the antibacterial effects. Removed tissue samples were fixed in a solution of 10% formalin in 100% PBS for 2 to 3 days. After fixation, samples were embedded in paraffin blocks, sectioned to a 6-µm thickness, and stained with hematoxylin-eosin and also with Gram stain. Stained slides were assessed under a light microscope (Olympus BX51 microscope) to observe any inflammation or gross tissue damage.

(vi) Statistical Methods.

Means were calculated and compared for statistical significance using a one-way analysis of variance (ANOVA). P values of <0.05 were considered statistically significant.

In reference to the above identified experiments, a mouse model of a partial-thickness skin wound (abrasion) was used to test the novel combination (RB plus KI and 540-nm light) in vivo. We chose *P. aeruginosa* as the bacterial pathogen for the following reasons: (i) *P. aeruginosa* is a Gram-negative bacterial species and would not be expected to be much affected by RB plus light alone (without KI), (ii) *P. aenuginosa* is sufficiently pathogenic to form a long-lasting infection with a reasonable infective dose of cells, and (iii) the particular strain of *P. aeruginosa* that we used is not sufficiently virulent in this model to cause a systemic infection, which would lead to death of the mice.

Figure 28:
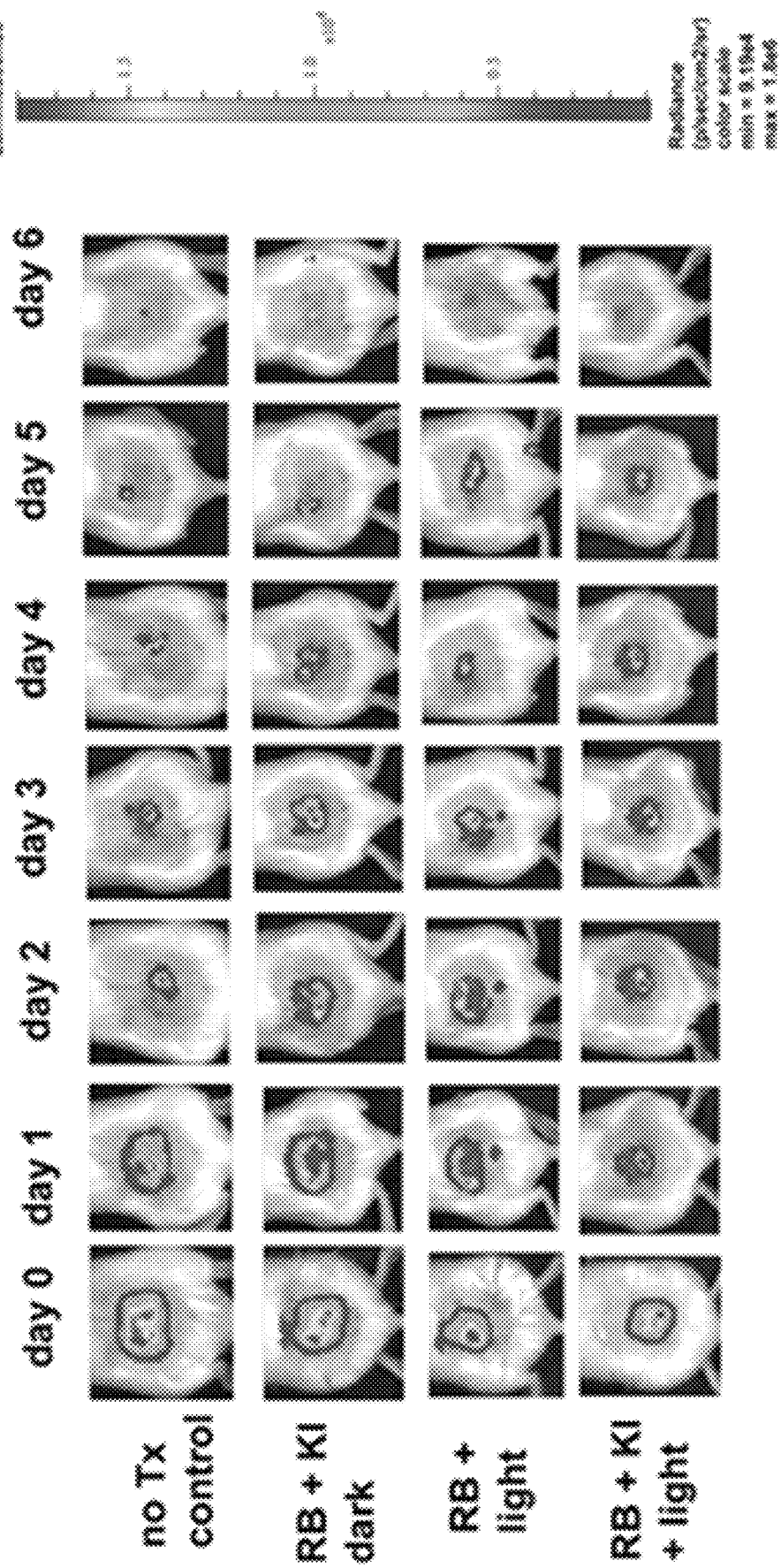
FIG. 28: Results of monitoring of aPDT of skin abrasions infected with *P. aenrginosa* in the days following light delivery. Images from representative mice from the four groups (for which the results are shown FIGS. 27A, 27B, 27C, 27D) were monitored for bioluminescence each day from day 0 (before PDT) until day 6. no Tx, no treatment.
Figure 29:
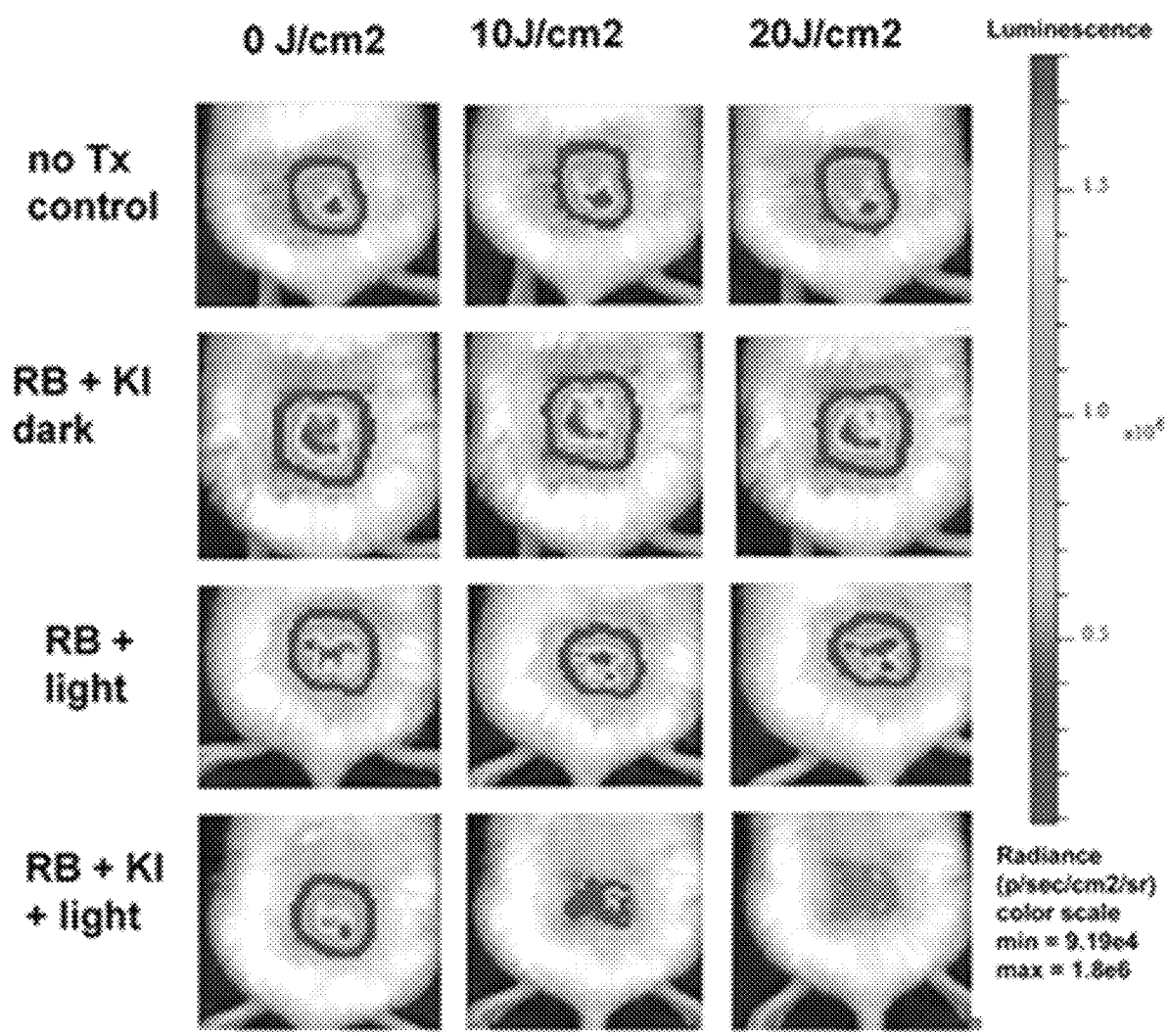
FIG. 29: Results of monitoring of aPDT of skin abrasions infected with *P. aeruginosa* during light delivery. Representative bioluminescence images from a mouse from each of the treatment groups are shown: the "no-treatment" control group; the group treated with 50 μl of RB (500 μM) plus KI (1 M) in the dark; the group treated with 50 μl of RB (500 μM) plus PDT; and the group treated with 50 μl of RB (500 μM) plus KI (1 M) and PDT. Images were captured after delivery of 0, 10, or 20 J/cm$^2$ of 540-nm light (image rows 3 and 4) or after equivalent times had elapsed (image rows 1 and 2).

When 5×10$^5$ CFU of bioluminescent *P. aenruginosa* (in 50 µl) was inoculated into the partial-thickness abrasion wound on the back of the mice, a stable infection that lasted for longer than 6 days was established. FIG. 28 shows results of the observations of representative mice from four groups for six successive days after PDT. It can be seen that there is not much difference between the groups. The only noticeable observation is that the signal from the RB plus KI and light group was significantly lower than that from each of the other three groups (P<0.05) on day 1 (i.e., the day immediately following PDT). FIG. 29 shows a panel of bioluminescence images from representative mice in each of the four groups captured before irradiation with light (0 J/cm$^2$), after irradiation with 10 J/cm$^2$ light at 520 nm, and after irradiation with 20 J/cm$^2$ of 540-nm light. The no-treatment control and RB plus KI dark groups (FIG. 29, rows 1 and 2) did not show any reduction in the bioluminescence signal, while the RB plus 540-nm light groups showed only a slight reduction. In contrast, the group treated with RB plus KI and 540-nm light showed a major reduction after 10 J/cm$^2$ was delivered, and after 20 J/cm$^2$ was delivered, the bioluminescence signal was undetectable.

Figures 30A, 30B:
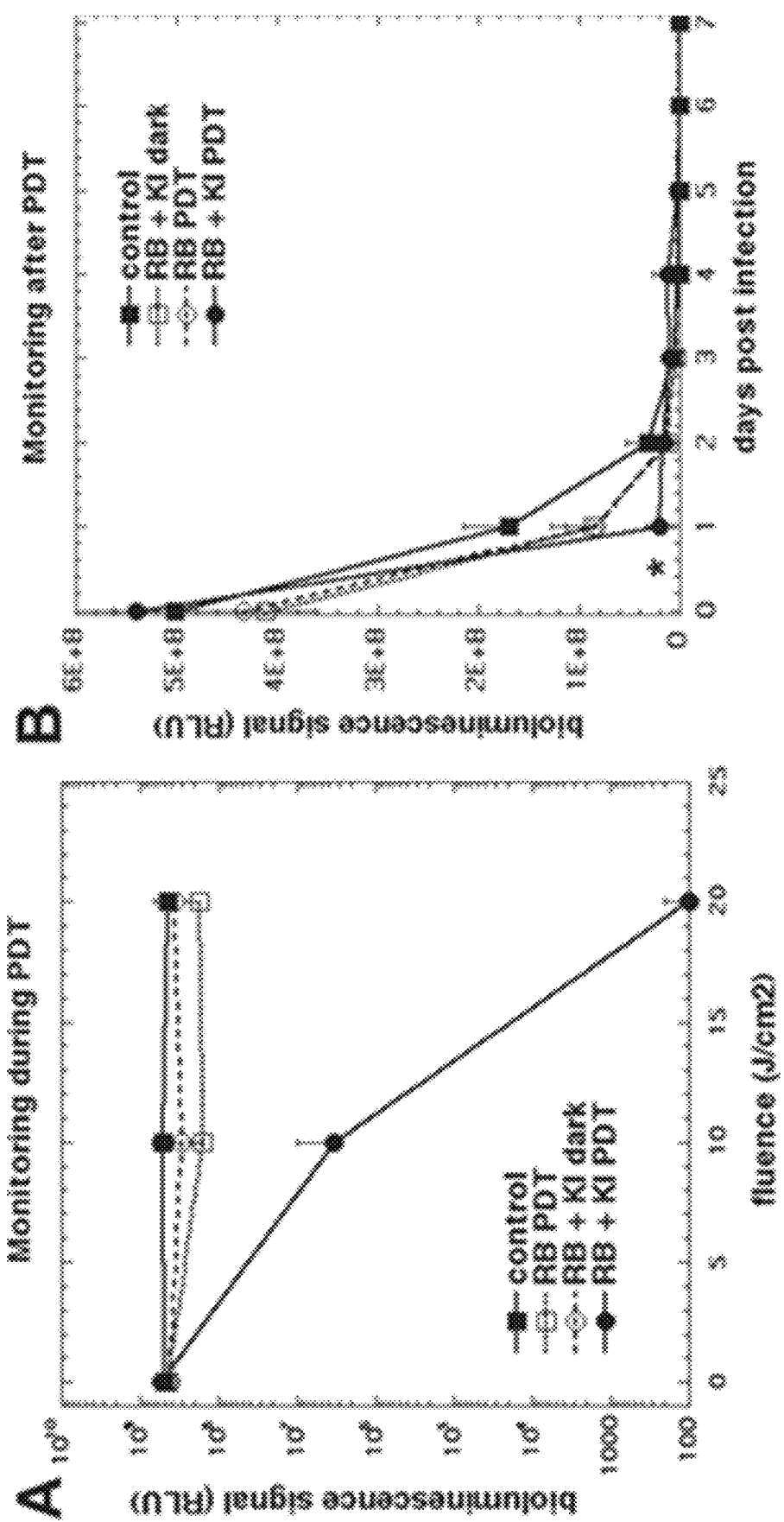
FIGS. 30A, 30B: Quantification of the bioluminescence signals from the mice in the groups for which the results are shown in FIGS. 28 and 29. Points represent mean values for 5 mice, and bars represent standard deviations. *, P<0.05 versus the control by one-way ANOVA.

FIG. 30A shows the quantification of the signals from 5 mice per group. FIG. 30B shows the quantification of the bioluminescence signals. The regrowth of the luminescence signal in the wound following the apparently successful eradication by PDT has been previously observed and is one of the drawbacks of using PDT as an antibacterial therapy in vivo.

Figure 31A:
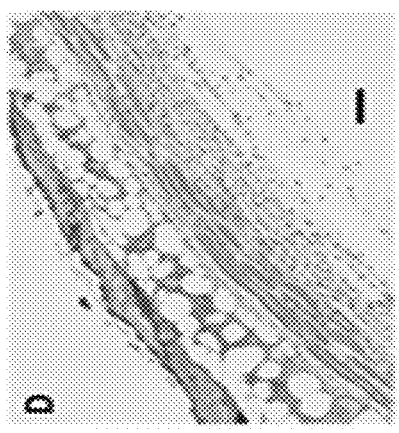
FIGS. 31A, 31B, 31C, 31D, 31E, 31F, 31G, 31H: Histology images.
Figure 31B:
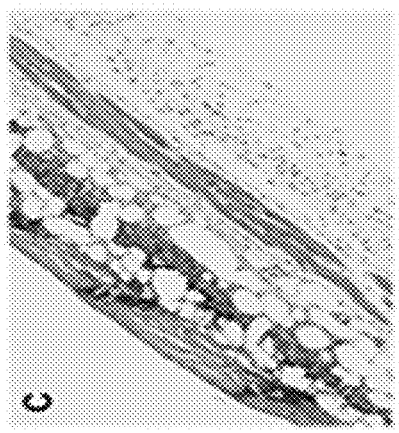
Figure 31C:
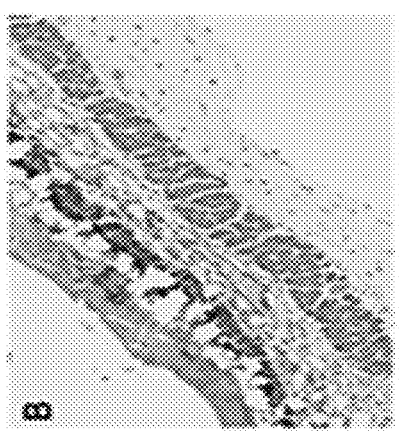
Figure 31D:
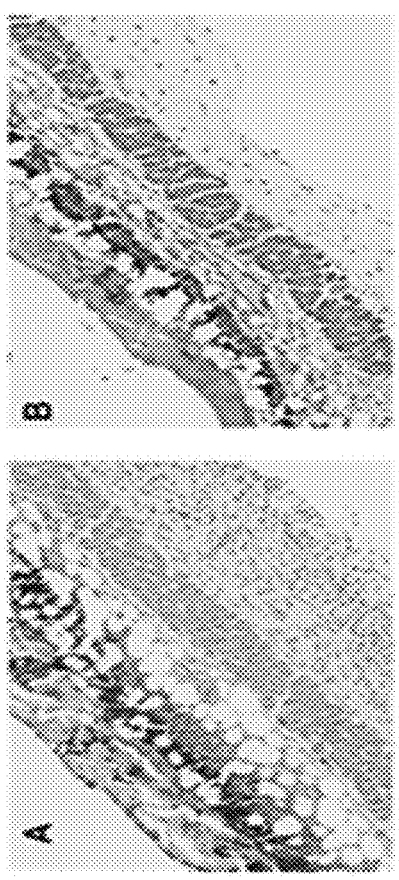
Figure 31E:
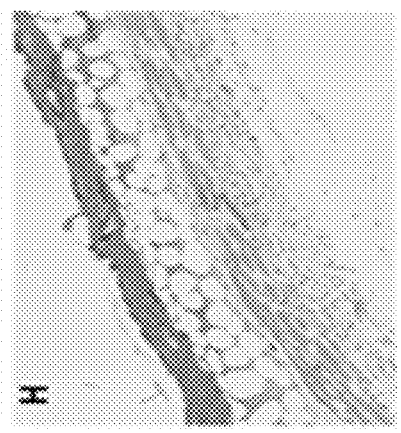
Figure 31F:
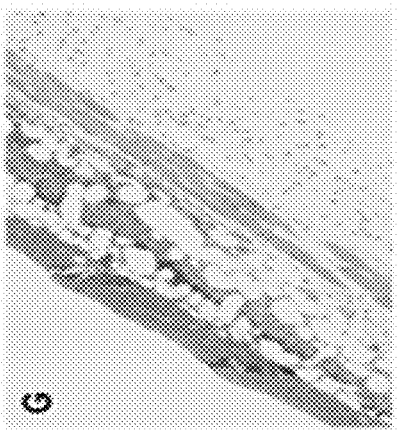
Figure 31G:
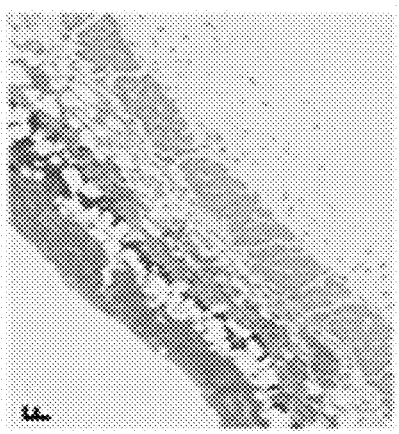
Figure 31H:
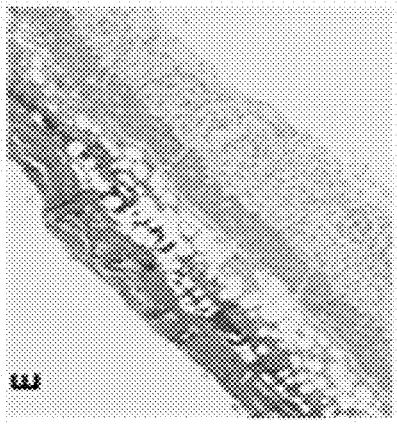

FIGS. 31A, 31B, 31C, 31D, 31E, 31F, 31G, and 31H are the histology images taken from mice that were sacrificed 24 h after the PDT. Here, the sections were stained with Gram stain to visualize the *P. aeruginosa* cells in the tissues (FIG. 31A to 31D) and also with hematoxylin and eosin (H&E) (FIGS. 31E to 31H) to visualize any gross damage that may have been caused by the PDT or by the iodine produced by PDT plus KI. There were clearly fewer bacteria present in the group treated with PDT plus KI (FIG. 31D) than in the other groups (FIG. 31A to 31C). While H&E staining is not necessarily the most sensitive method to detect PDT-induced tissue damage, there were no obvious signs of extra damage in FIG. 31H compared to FIGS. 31E to 31G.

Results Illustrating Potentiating Effect, Produced by Addition of Salt of Alkaline Material to RB, on Bacterial Killing.

Based on the above demonstrations, a person of skill will readily appreciate that addition of the simple nontoxic inorganic salt potassium iodide can dramatically potentiate aPDI mediated by RB, especially against Gram-negative bacteria. In the case of two Gram-negative bacterial species, *E. coli* and the hard-to-kill species *P. aeruginosa*, addition of 25 mM KI gave 7 logs of killing, whereas almost no killing was obtained with RB aPDI in the absence of KI. In the case of the fungal yeast *C. albicans*, addition of 100 mM KI gave eradication (>6 logs of killing), whereas just over 1 log of killing was achieved without KI.

The data suggest that two kinds of antimicrobial species are produced by the PDT-induced oxidation of iodide. The most obvious antimicrobial species is molecular iodine (or triiodide in the presence of iodide), as shown by the generation of the blue inclusion complex when starch was added to the reaction product obtained when 540-nm light was delivered to a mixture of RB plus KI. Nevertheless, there is clearly another short-lived antimicrobial species that is generated and can produce killing only when the cells are present during the illumination. With Gram-negative bacteria, eradication was achieved with 25 mM KI when cells were present, while 100 mM KI was necessary when the bacteria were added after light. In the case of *C. albicans*, eradication was achieved with 100 mM KI when cells were present, while hardly any killing was seen when cells were added after light. In the case of methicillin-resistant *Staphylococcus aureus* (MRSA) (with a low concen-tration of RB and 100 mM KI), eradication was achieved with the cells were present and only 1 log of killing was achieved when cells were added after light. The explanation for the difference in susceptibility between Gram-negative species, on the one hand, and Gram-positive species and *Candida*, on the other hand, when cells were added after light probably lies in features such as the thickness of the cell wall. The thin cell wall typical of Gram-negative bacteria may allow iodine species to penetrate and kill them with an ease greater than that found with other microbial cells with thicker cell walls.

RB does not bind well to most classes of microbial cells. This lack of binding is shown by the fact that centrifugation of the cells after incubation with RB removes most, if not all, of the light-mediated killing. Even with the Gram-positive bacterium MRSA, against which RB is extremely active as an antimicrobial PS (since the low concentration of 200 nM produced eradication), centrifugation abolished the killing. In the case of *C. albicans*, binding appears to be of some importance, since there was some minor killing after centrifugation; there was also potentiation with 100 mM KI when cells were present but no killing when cells were added after light. As seen in FIGS. 3A, 3B, *C. albicans* was the only cell type to show any detectable fluorescence after incubation with RB. We assume that the reactive iodine species are more efficient in killing microbial cells when they are generated close to the cells, as might be expected with loose binding of the RB to the cell surface. If the binding between the cells and the RB was loose, it might be expected that the RB could be dislodged after centrifugation.

RB was found to operate largely via the type II photochemical pathway involving energy (hv) transfer from the long-lived RB triplet state to the ground-state triplet oxygen to produce the reactive singlet oxygen (equations 1 and 2, below). The number of heavy halogen atoms (4 iodine and 4 chlorine atoms) means that RB has a singlet oxygen quantum yield of about 0.86. In fact, RB is often used as a standard in determinations of singlet oxygen quantum yields.

$$^1RB + h\nu \rightarrow {^3RB} \tag{1}$$

$$^3RB + {^3O_2} \rightarrow {^1RB} + {^1O_2} \tag{2}$$

There two possible pathways by which singlet oxygen could, in principle, react with iodide anion. The first pathway is a one-electron transfer from iodide to $^1O_2$ to give superoxide anion and iodide radical (equation 3):

$$^1O_2 + I^- \rightarrow O_2^{\cdot-} + I\cdot \tag{3}$$

The iodide radicals dimerize to give molecular iodine, which reacts with iodide to give the triiodide anion (equation 4). Iodine radicals would then be the short-lived reactive species that give potentiation of aPDI killing.

$$2I\cdot + I^- \rightarrow I_3^- \tag{4}$$

The superoxide anion then undergoes dismutation to give hydrogen peroxide (equation 5).

$$2O_2^{\cdot-} + 2H^+ \rightarrow H_2O_2 + O_2 \tag{5}$$

This pathway was our initial hypothesis, after we demonstrated the formation of both iodine/triiodide and hydrogen peroxide, which was consistent with the proposed mechanism. However, despite numerous attempts, we were unable to show any production of superoxide using the NBT assay, even though we were able to obtain a positive result with another established photochemical method to generate superoxide. This was done by illumination of a water-soluble fullerene in the presence of reduced NADH. Hence, we concluded that a one-electron transfer reaction from iodide to singlet oxygen to give superoxide and the iodine radical probably did not occur. It must also be stressed that such a reaction is thermodynamically unlikely, for it would be accompanied by an unfavorable change in free energy. This is because the one-electron reduction potentials of the corresponding couples, $^1O_2/O_2^{\cdot-}$ and $I\cdot/I^-$, are +0.65 V and +1.270 to 1.400 V, respectively.

However, there is a second possible pathway between singlet oxygen and iodide. This takes the form of an addition reaction between singlet oxygen and iodide to give peroxyiodide (equation 6).

$$^1O_2 + I^- + H_2O \rightarrow IOOH + HO^- \tag{6}$$

The decomposition of peroxyiodide is proposed to proceed via equations (7) to (10):

$$IOOH + I^- \rightarrow HOOI_2^- \tag{7}$$

$$HOOI_2^- \rightarrow I_2 + HO_2^- \tag{8}$$

$$I_2 + I^- \rightarrow I_3^- \tag{9}$$

$$HO_2^- + H_2O \rightarrow H_2O_2 + HO^- \tag{10}$$

As described by Dalmazio et al. (in J. Braz. Chem. Soc. 19:1105-1110; 2006), the mass spectrometry and ab initio free energy calculations were used to study the decomposition of hydrogen peroxide in the presence of iodide anions. Detected were the species with m/z 287 that was proposed to be $HOOI_2^-$. Calculations revealed that the thermodynamically preferred decomposition pathway was equation (11) to produce two radicals:

$$HOOI_2^- \rightarrow I_2^{\cdot-} + HOO\cdot \tag{11}$$

Competing decomposition pathways were energetically less favored by between 25 and 68 kcal/mol.

These two radicals, $I_2^{\cdot-}$ and HOO·, would account for the short-lived reactive species responsible for the extra killing observed when the cells were present during the illumination.

In our related disclosures we originally discovered that the action of KI (maximum concentration, 10 mM) potentiates the aPDI mediated by the phenothiazinium salt methylene blue (MB) (16). We had previously shown that the potentiation of aPDI mediated by MB was paradoxically potentiated by 10 mM sodium azide (singlet oxygen quencher) operating by a one-electron transfer from azide anion to excited state MB to form azide radicals in an oxygen-independent process. Therefore, we assumed that the mechanism in the case of KI and MB was an analogous one-electron transfer from the iodide anion to the excited-state PS to form an iodine radical and an MB radical anion. We then went on to show that the photocatalysis mediated by titanium dioxide nanoparticles excited by UV-A light could also be strongly potentiated by addition of KI. Here the mechanism was via a mixture of a one-electron oxidation of iodide anion to form molecular iodine and a two-electron oxidation of iodide anion to form hypoiodite. It was not until we discovered that aPDI mediated by the porphyrin PS known as Photofrin was also able to be strongly potentiated by KI (provided the concentration of iodide was at least 25 mM and, preferably, 100 mM) that we realized singlet oxygen was likely to be involved in the process. We were able to show not only that activation of SOSG was quenched by KI but also that the luminescence signal of singlet oxygen was quenched by iodide and that oxygen was consumed in irradiated samples containing RB and KI. Quenching of the characteristic singlet oxygen phosphorescence by KI suggests that the effect is due to the interaction of KI with singlet oxygen, which shortens the observable lifetime of singlet oxygen, and to the interaction of KI with the RB triplet excited state, which reduces the observable intensity of singlet oxygen. While the former interaction is mostly chemical in nature, leading to the formation of the unstable peroxyiodide, the latter interaction could be a physical quenching of the RB triplet excited state with no specific product formed or a charge-coupled triplet deactivation, in which the triplet excited state of RB is reduced by KI. Although it was earlier reported on a very efficient quenching of both the singlet and triplet excited states of pteridines by KI, with the corresponding rate constants being close to the diffusion-controlled limit, the effect observed in the present study (FIG. 27A) suggests that the efficiency with which KI quenches the RB excited triplet state is significantly lower. This is probably due to the strong electrostatic repulsive interaction of the two molecules, which in water at neutral pH are negatively charged, and to the relatively low energy level of the RB triplet excited state that makes the charge-coupled quenching mechanism inefficient.

In the present study, we were able to show the effectiveness of KI as an enhancer of RB-mediated PDT in a mouse model of a partial-thickness wound infection caused by the stubborn and drug-resistant Gram-negative bacterial pathogen P. aeruginosa. Although MRSA is the most problematic cause of complicated skin and soft tissue infections (SSTIs), P. aenginosa comes in second in this regard. Moreover, P. aenginosa displays intrinsic antibiotic resistance, has the capacity to acquire further resistance mechanisms, and readily forms a protective biofilm in vivo. Among several studies of aPDI, P. aeruginosa is considered to be one of the hardest bacterial species to kill by aPDI. The monitoring of the bioluminescence signal during light delivery did show a strong potentiation of the bactericidal effect by addition of KI, as might be expected from the m vitro data. Moreover, the monitoring of the bioluminescence signal in the days following PDT appeared to show that the addition of KI also appeared to give some benefit in inhibiting recurrence, especially on the day after PDT. It has become apparent that the main drawback to using PDT as an antibacterial intervention in models of localized infection is the fact that after the light has been turned off, the generation of antimicrobial species ceases and any remaining bacteria are completely free to regrow. However, in the present case of added KI, it is likely that free iodine/triiodide is generated within the wound by the action of photogenerated singlet oxygen on iodide anions. This free iodine/triiodide may remain active within the wound for a much longer time and may inhibit bacterial regrowth for some time to come.

Additional Examples of Use of the Method for Potentiating the PDL

It is appreciated that the use of embodiments of PDI-processes (employing complex MCPPS's of the invention to increase potency of the PDI) in combination with various medical/dental tools and specifically-designed photonic systems (such as those, for example, described in WO 2014/004752) is within the scope of the invention.

For example, practical uses of potentiation of photoactivated titania with a salt of alkaline metal can be envisioned to depend on whether the salt is free in solution around the titania, or whether the salt is packaged together with the titania nanoparticles in some sort of hybrid nanostructure. In one form, according to an embodiments of the invention, such hybrid nanostructure (referred to herein as a "nanocell") is similar to a liposome, and includes a vesicle formed from a spherical lipid bilayer, but instead of containing a just an aqueous interior like a regular liposome, the nanocell encapsulates one or more nanoparticles (such as $T_iO_2$ P25) and an aqueous solution of the salt (such as 100 mM KI, for example). Such nanocell would release reactive iodine species after being photoactivated. It another embodiment, a hybrid nanostructure including a $T_iO_2$ nanoparticle coated with an insoluble iodide salt (for instance silver iodide) is created to form a slightly bigger nanoparticle. The applications of this technology include photoactivated antimicrobial surfaces, where the iodide solution is most likely to be used. Here, just before the surface is activated by light, a solution of iodide is sprayed onto the material. When used with implantable medical devices, such as artificial joints or any indwelling device (such as endotracheal tubes, catheters or access ports, to name just a few), such approach allows for sterilization of the devices without the need to removal from tissue via surgery. While typically the sterilization process is difficult without unacceptable damage to the surrounding tissue, the embodiment of the invention includes a device already pre-coated with $T_iO_2$, while the solution of the identified salt and PDI-process-triggering light are delivered to the surface of the device. In a related embodiment, the same approach is used in dentistry for sterilization of root canals (endodontics) where the combination of $T_iO_2$ and the potentiating salt could be added into the canal and activated with light (via a fiber-optic cable, for example). Nasal decontamination of MRSA is another application where a gel containing both $T_iO_2$ and the potentiating salt is rubbed inside the nose followed by light activation. In cases where hybrid nanostructures are used, these can be made to be injectable. For instance the $T_iO_2$/salt nanocells could be injected into tumors, into sites with localized infections (abscesses), or into tissue that is required to be destroyed. Light could be delivered via a fiber optic to activate the system.

Figure 16:
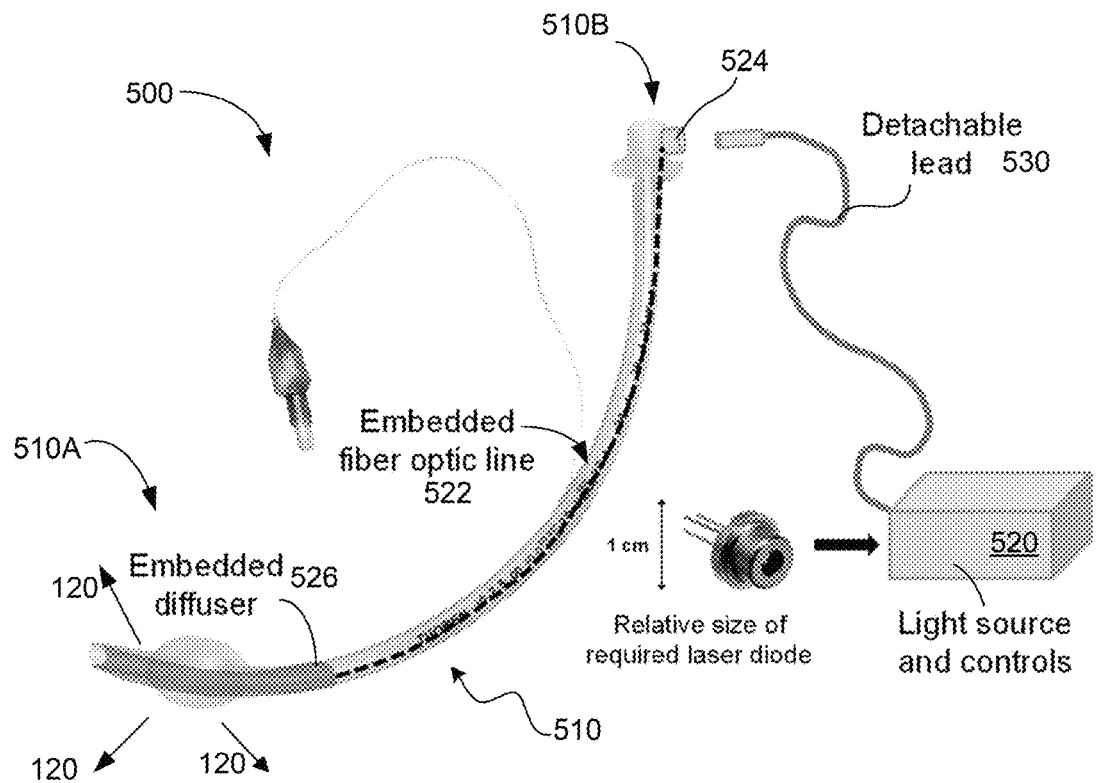
FIG. 16 is a schematic diagram of a device for use with a method of the invention.

In a related embodiment, the method of the invention is practiced with a photonic system such as a catheter specifically-structured to contain in its body a passage, through which the multi-component photosensitizer material is delivered to the targeted area (in a form of a solution, for example) and a fiber-optic (FO) cable or waveguide, through which the triggering light is guided to the region of interest (ROI) where the delivered material is located. One example 500 of such catheter is shown in FIG. 16 and described in detail in WO2014/004752, the entire disclosure of which is incorporated herein by reference. Here, the device of the invention has a tubular wall and includes a catheter or tube or stent or shunt 510 having distal and proximal ends 510A, 510B and a source of excitation power 520 that is external to and, optionally, removably connectable to the proximal end 510b of the tube 510 via a detachable lead 530. The catheter or tube 510 contains an optical fiber line (or, alternatively, a channel waveguide line) 522 embedded in the tube 510, a port 524 of which is adjacent to and/or cooperated with the proximal end 510b. The catheter or tube 510 also contains an optically-diffusing element 526 implanted or embedded in or at the distal end 510A. In one embodiment, the light-diffuser 526 and/or the tube 510 is adapted to form a substantially spatially-uniform distribution of light output. The source 520 (such as, for example, a light source and electronic circuitry adapted to effectuate the operation of the light source) transmits the excitation power (in one embodiment—the electro-magnetic radiation and, in particular, light), through the lead 530 towards the port 524, when connected, and further down the fiberoptic line 522 towards the diffuser 526. The diffuser 526 outcouples light 120 towards the surrounding medium in which the distal end 510a is inserted or implanted. While the optical fiber line 522 is generally passing through and along the wall of the tuber 510, in a specific embodiment shown in FIG. 6 such line 522A is structured as a three-dimensional spiral extending, in the wall of the tube 510, between the proximal and distal ends 510A, 510B and establishing optical communication between the port 524 and the diffuser 526. The spiral-shaped fiber optic line 522 is, optionally, built in the wall of the tube 510 during the process of tube manufacturing. Alternatively, the fiber optic line 522 is wound or coiled around an existing tube and overcoated (to laminate the line 522) with a plastic overlayer the properties of which (including mechanical properties and biocompatibility) are similar to those of the material of the tube 510. In a related embodiment (not shown), no separate FO-cable may be required, and the walls of the catheter itself (its sheath, for example) are configured to guide light towards a region of interest (ROI) where the target bacteria are located.

In another related embodiment, the implementation of invention as discussed in Example 1 was extended to in vivo studies in a murine infection model of burn and carried out with the use of bioluminescent MRSA and in vivo imaging. The goal here was to verify the increase of the efficacy of PDI-process of bacterial killing by adding KI to MB in an in vivo infection model.

Figures 17A, 17B, 17C, 17D, 17E:
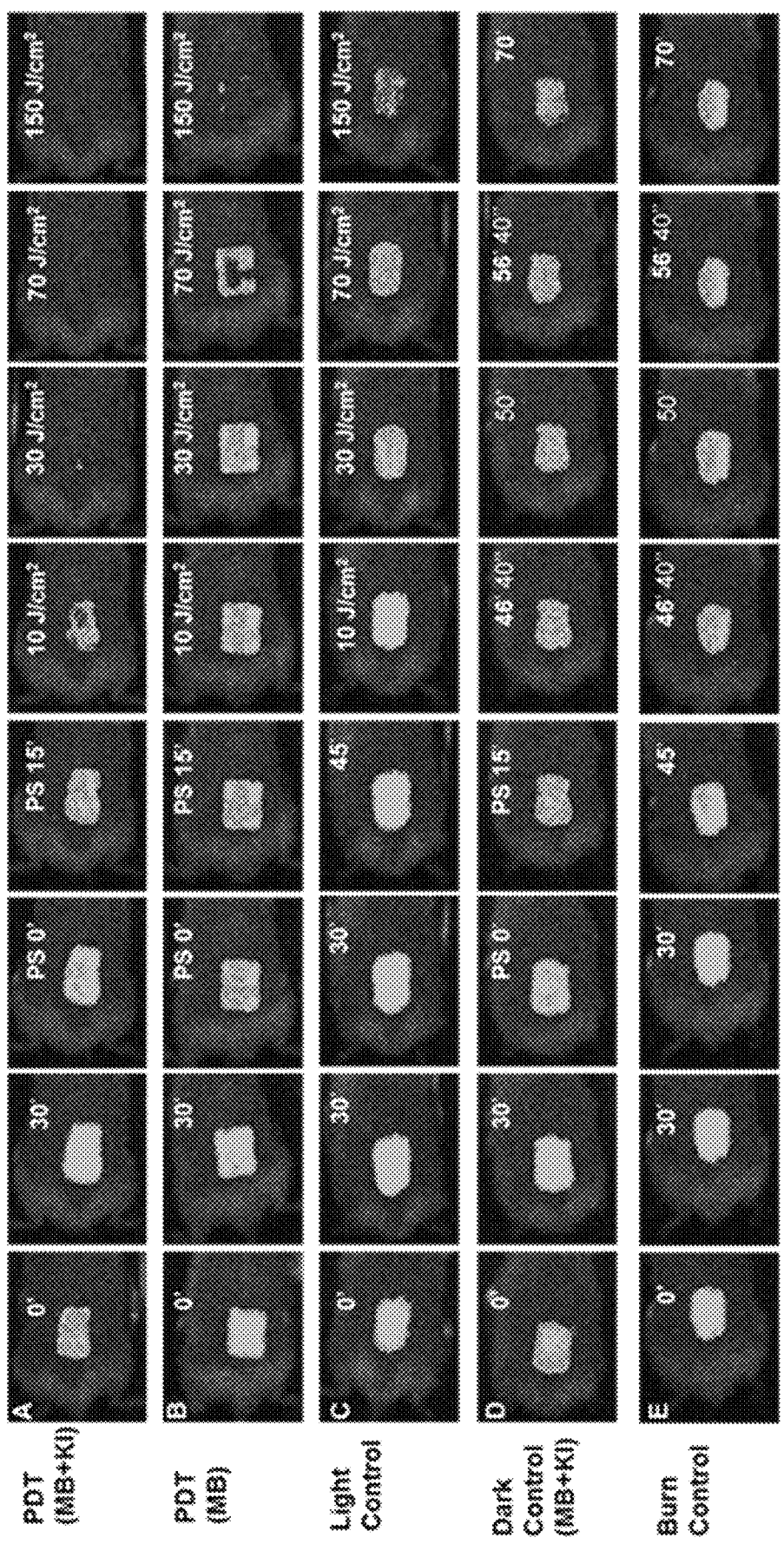
FIGS. 17A, 17B, 17C, 17D, 17E represent a set of bioluminescence images, each taken over time, of a burn infected with MRSA and treated according to an embodiment of the invention.

In reference to FIGS. 17A, 17B, 17C, 17D, 17E the infected burn was treated with 50 μM of MB, with and without the addition of 10 mM of KI and excited with 660 nm light; up to 150 J/cm$^2$ while the control groups were dark controls with the same amount of MB+KI and light alone control received 660 nm light to 150 J/cm$^2$. Aggregately, FIGS. 17A through 17E represent a set of 5 representative bioluminescence image time courses from the burn (each time course from a single mouse in each of the 5 groups) infected with MRSA. The bacterial bioluminescence was largely preserved in the infected burn control (FIG. 17E) during the treatment with light alone (FIG. 17C) and in dark controls of MB+KI (FIG. 17D). In contrast, PDI gave a light dose-dependent reduction of bacterial bioluminescence from mice wounds treated with MB (FIG. 17B) or MB+KI (FIG. 17A) during the PDI treatment. The amount of light required to eradicate bacteria from the wound was much less when the bacteria treated with the (MB+KI) solution was irradiated than when MB alone was used to pre-treat bacteria prior to irradiation.

Figure 18:
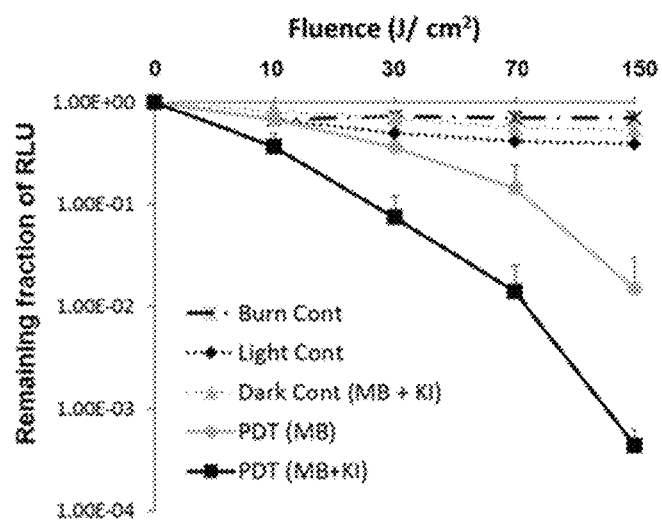
FIG. 18 provides the light-dose-response curves for all groups of FIGS. 17A through 17E.

FIG. 18 provides the light-dose-response curves of all groups. Each curve represents the average±SEM of bacterial bioluminescence in each group (n=6). PDI using MB induced a decrease of around 2 log unit in bacterial bioluminescence while the MK+KI induced up to 3.5 log unit reductions during the same time.

Figures 19A, 19B, 19C, 19D, 19E:
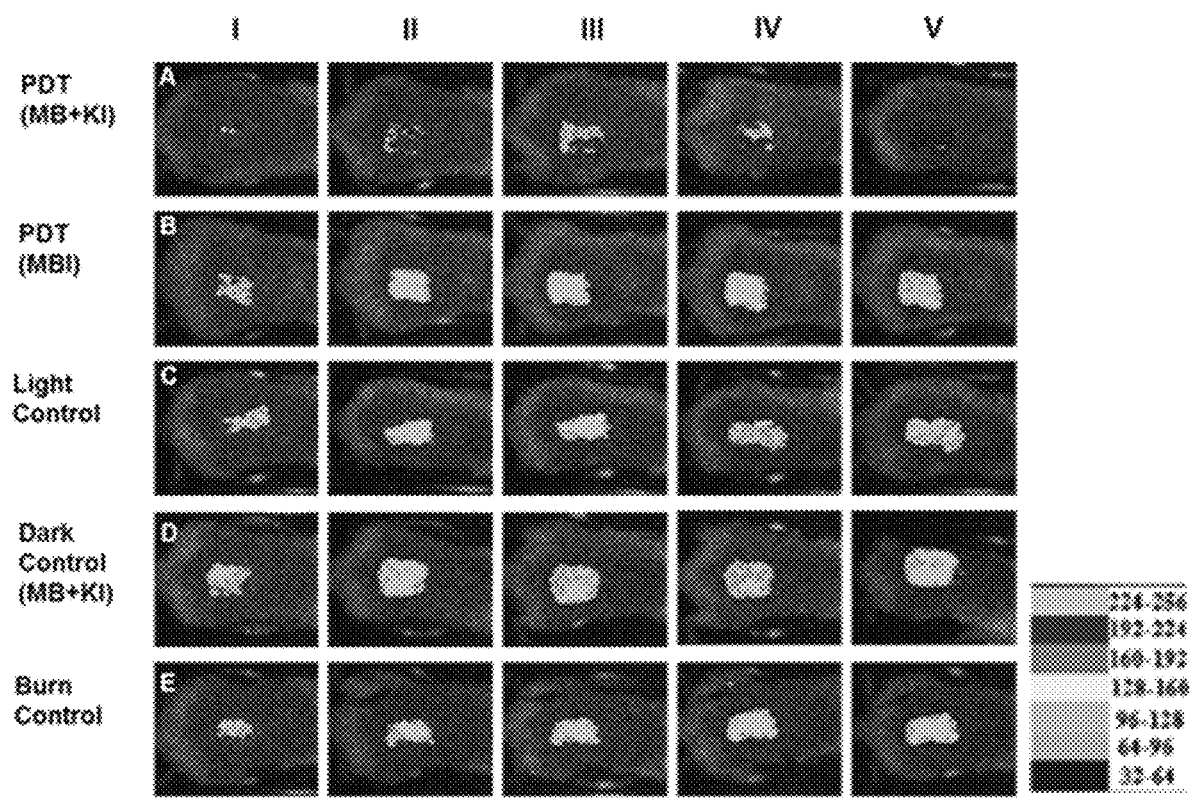
FIGS. 19A, 19B, 19C, 19D, 19E, 19F, 19G illustrate the results of the follow-up monitoring of burns of FIGS. 17A through 17E after the PDI procedure was concluded.
Figure 19G:
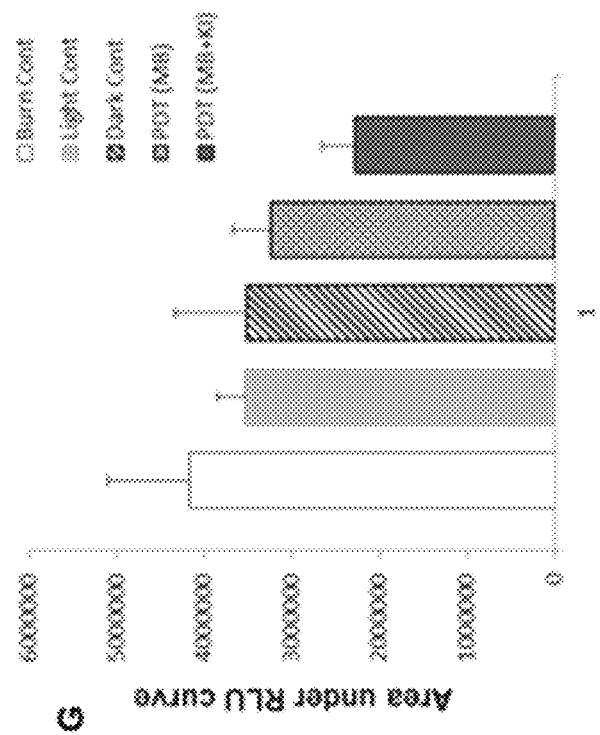
Figure 19F:
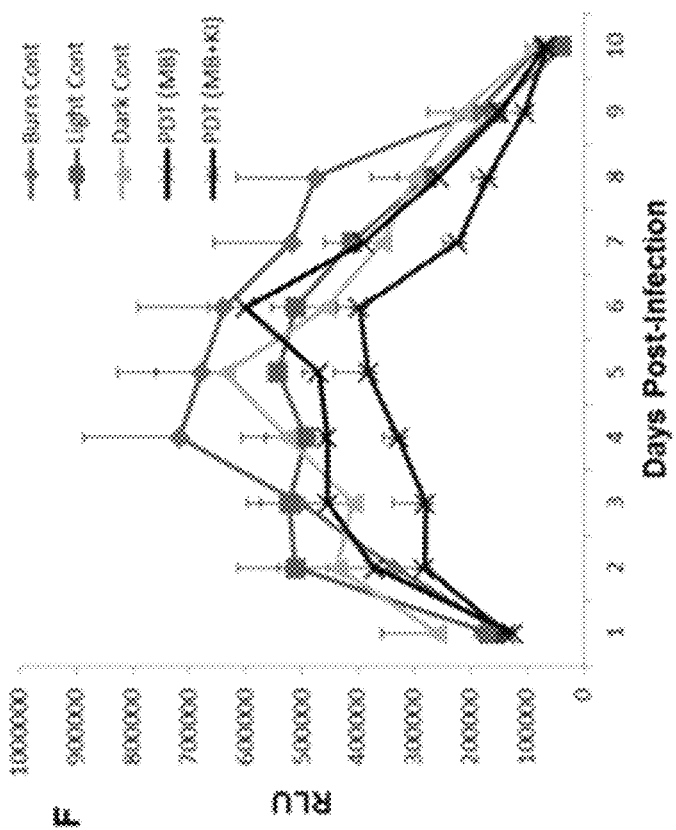

FIGS. 19A, 19B, 19C, 19D, 19E, 19F, 19G illustrate the results of the follow-up monitoring of the bioluminescence images (time courses over 5 days) after the PDI in representative mice from all groups. Consistent differences were observed in bacterial re-growth between PDI performed by using MB+KI (FIG. 19A) and the other groups (FIGS. 19B, 19C, 19D, 19E). In the first case the bacterial re-growth was minimal in that the presence of KI increased the efficacy of PDT at the first treatment to produce sufficient bacterial killing to reduce the recurrence observed during the days post infections, when PDI mediated with the MB alone was not effective to prevent recurrence. The time courses (from day 0 to day 10) of the mean bacterial bioluminescence signal of infected wounds in the different groups of mice are shown in FIG. 19F. The areas under the curves (FIG. 19G) were compared and PDI potentiated with the mix of MB and KI (group E) was significantly lower than all other groups.

Figures 20A, 20B, 20C, 20D:
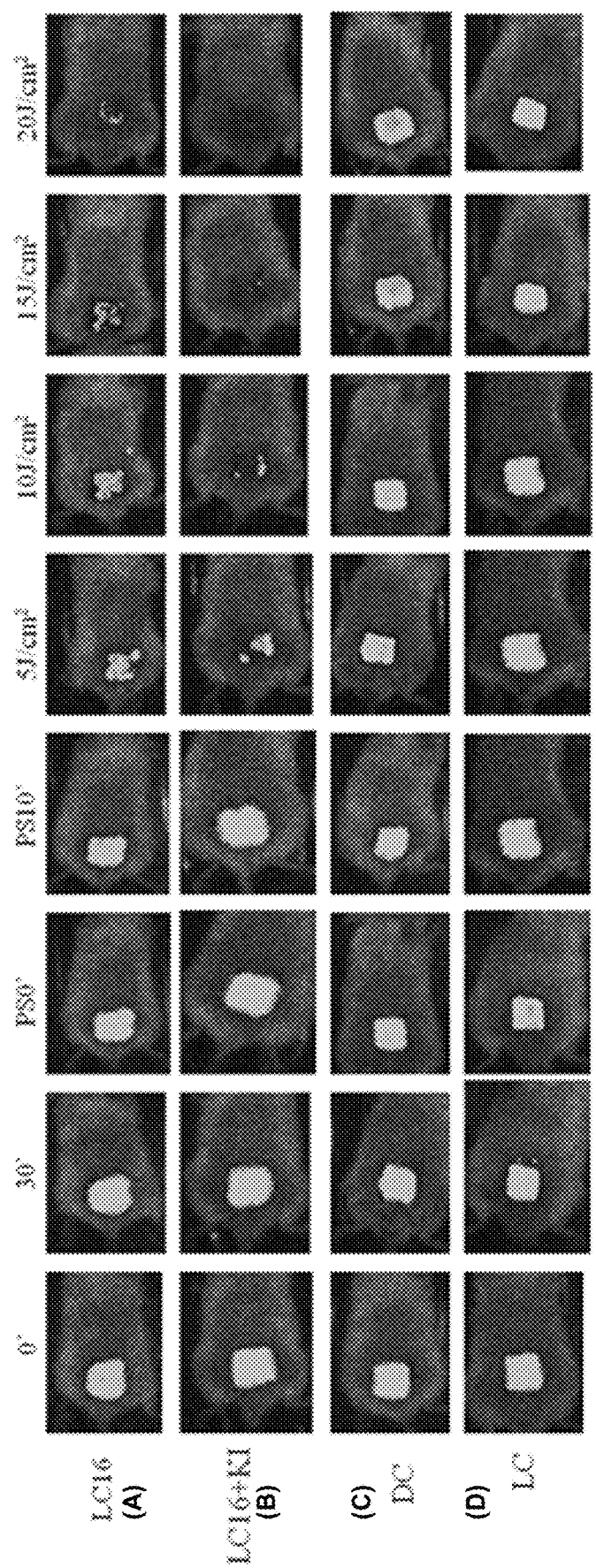
FIGS. 20A, 20B, 20C, 20D are illustrations of complete elimination of the bioluminescence signal as a result of PDI-treatment of a biological tissue with UVA light, mediated with a combination of LC16 and KI.
Figures 21A, 21B, 21C, 21D:
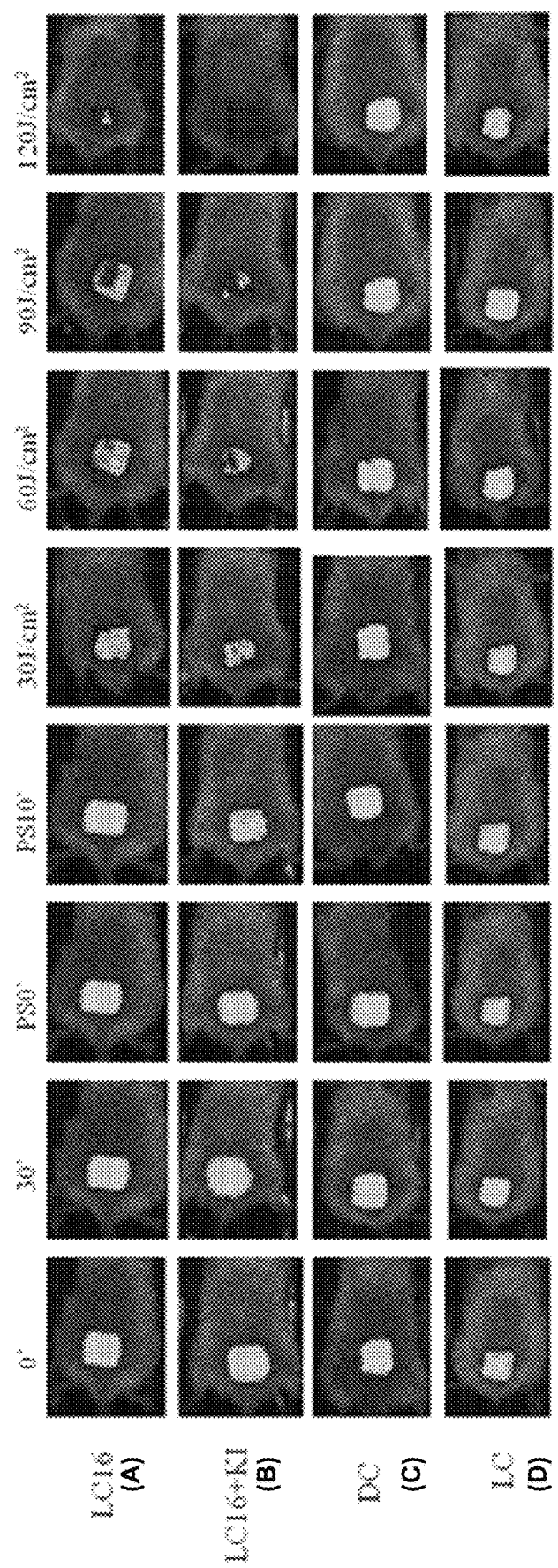
FIGS. 21A, 21B, 21C, 21D are illustrations of complete elimination of the bioluminescence signal as a result of PDI-treatment of a biological tissue with white light, mediated with a combination of LC16 and KI.

In yet another related embodiment, the experiments described in Example 2 were extended to in vivo studies. Here, thirty minutes after application of the bacteria to the abrasions, The infected abrasion was treated with 200 μM of LC16, with and without the addition of 10 mM of KI and excited with UVA light up to 20 J/cm$^2$ while the control groups were dark controls with the same amount of LC16+KI and light alone control received UVA light to 20 J/cm$^2$. The results are shown in FIGS. 20A, 20AB, 20C, 20D, from which it can be seen that a complete elimination of the bioluminescence signal was observed after a UVA dose of 20 J/cm$^2$ was delivered in the presence of LC16+KI. However the LC16+UVA group without added KI still had bioluminescence signals remaining in the wound. Both light and dark controls had no measurable diminution in bioluminescence signal during the course of the experiment.

The results of the experiment using white light to excite the fullerene/iodide combination are shown in FIGS. 21A, 21B, 21C, 21D. The loss of bioluminescence signal was slightly less pronounced after excitation with 120 J/cm2 than it was with 20 J/cm2 UVA light. Nevertheless the addition of iodide also gave a much better bacterial killing when LC16 was excited by white light.

Figure 22A:
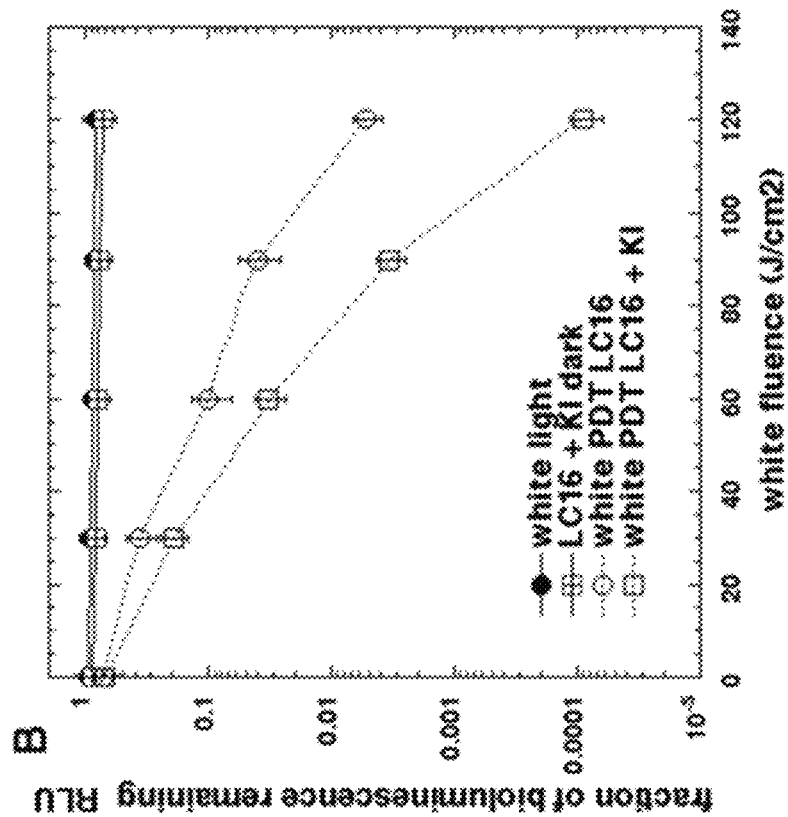
FIGS. 22A and 22B display the light-dose-response curves of the fraction remaining of the normalized bioluminescence signals calculated from the different groups of tissue in vivo.
Figure 22B:
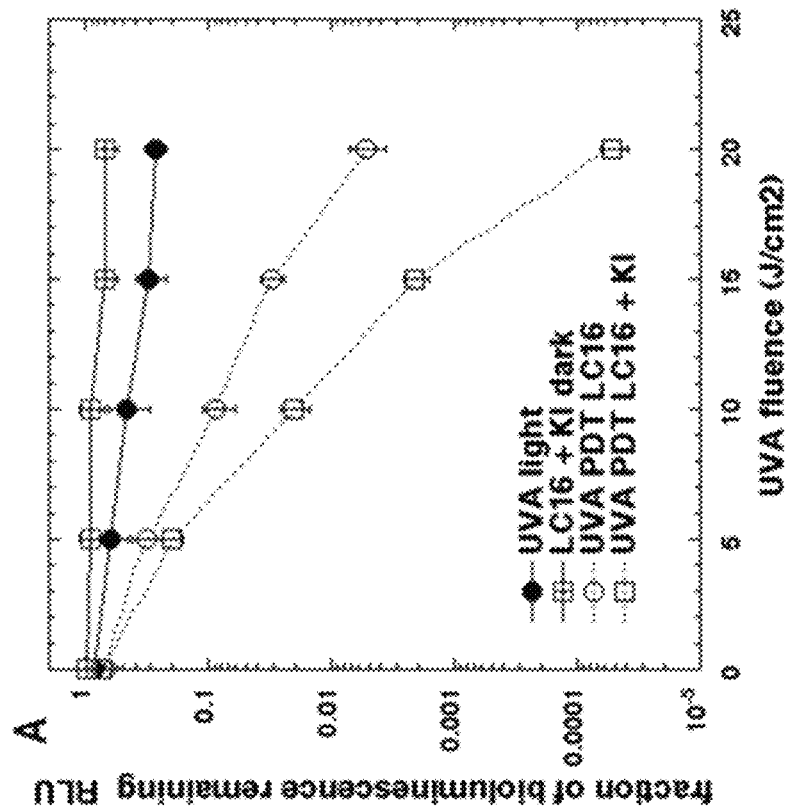

FIGS. 22A and 22B show the light-dose-response curves of the fraction remaining of the normalized bioluminescence signals calculated from the different mouse groups. When UVA was used for excitation of LC16+KI it gave a reduction of over 4-logs while LC16+UVA alone (no KI) gave a reduction of only 2-log of the bioluminescence RLU ($p<0.001$). No significant reduction was seen for either dark or light control. PDT mediated white light excitation of LC16+KI induced a reduction of ca. 4-log in RLU, while LC16 alone+white light gave a reduction of only 2-log of the bioluminescence RLU ($p<0.001$).

References throughout this specification to "one embodiment," "an embodiment," "a related embodiment," or similar language mean that a particular feature, structure, or characteristic described in connection with the referred to "embodiment" is included in at least one embodiment of the present invention. Thus, appearances of the phrases "in one embodiment," "in an embodiment," and similar language throughout this specification may, but do not necessarily, all refer to the same embodiment. It is to be understood that no portion of disclosure, taken on its own and/or in reference to a figure, is intended to provide a complete description of all features of the invention.

In addition, in drawings, with reference to which the following disclosure may describe features of the invention, like numbers represent the same or similar elements wherever possible. In the drawings, the depicted structural elements are generally not to scale, and certain components are enlarged relative to the other components for purposes of emphasis and understanding. It is to be understood that no single drawing is intended to support a complete description of all features of the invention. In other words, a given drawing is generally descriptive of only some, and not all, features of the invention. A given drawing and an associated portion of the disclosure containing a description referencing such drawing do not, generally, contain all elements of a particular view or all features that can be presented is this view in order to simplify the given drawing and the discussion, and to direct the discussion to particular elements that are featured in this drawing.

A skilled artisan will recognize that the invention may possibly be practiced without one or more of the specific features, elements, components, structures, details, or characteristics, or with the use of other methods, components, materials, and so forth. Therefore, although a particular detail of an embodiment of the invention may not be necessarily shown in each and every drawing describing such embodiment, the presence of this detail in the drawing may be implied unless the context of the description requires otherwise. In other instances, well known structures, details, materials, or operations may be not shown in a given drawing or described in detail to avoid obscuring aspects of an embodiment of the invention that are being discussed. Furthermore, the described features, structures, or characteristics of the invention may be combined in any suitable manner in one or more embodiments.

Moreover, if the schematic flow chart diagram is included, it is generally set forth as a logical flow-chart diagram. As such, the depicted order and labeled steps of the logical flow are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow-chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Without loss of generality, the order in which processing steps or particular methods occur may or may not strictly adhere to the order of the corresponding steps shown. The invention as recited in the appended claims is intended to be assessed in light of the disclosure as a whole.

What is claimed is:

1. A method for photodynamic inactivation of target bacteria, the method comprising:
   intermixing first and second compositions of matter to form a mixture of the first and second compositions of matter;
      wherein the first composition of matter comprises a single-component photosensitizer (PS) having a first efficiency in mediating said photodynamic inactivation on its own in absence of the second composition of matter, the first composition of matter including rose bengal,
      wherein the second composition of matter includes an iodide salt of an alkaline metal and has no efficiency in mediating said photodynamic inactivation on its own in absence of the first composition of matter;
   treating said bacteria to form a first amount of treated bacteria by establishing contact between said mixture and said target bacteria; and
   for a pre-determined duration of time, irradiating said first amount of treated bacteria with light having a wavelength to reduce the first amount of treated bacteria,
      wherein said wavelength is chosen to trigger said process when said target bacteria has been treated with only the single-component PS.

2. A method according to claim 1, wherein said intermixing includes intermixing a first solution of said first composition of matter and a second solution of said second composition of matter.

3. A method according to claim 1, wherein said method includes applying the second composition of matter to the first composition of matter carried by a support surface.

4. A method according to claim 1,
   wherein said irradiating includes reducing the first amount with second efficiency of M>N;
   wherein N is equal to said first efficiency.

5. A method according to claim 4, wherein M/N is at least 10.

6. A method according to claim 4, wherein M/N is at least 100.

7. A method according to claim 4, wherein M/N is at least 1,000.

8. A method according to claim 1, wherein said treating includes establishing contact of said mixture of the first and second compositions of matter with said target bacteria carried by a surface of at least one of a dental tool, a surgical tool, and a surface in a clinical environment.

9. A method according to claim 1, wherein said treating includes transporting said mixture of the first and second compositions of matter along a delivery channel of a catheter to a distal portion of the catheter.

10. A method according to claim 9, wherein said irradiating the first amount of treated bacteria includes transmitting said light along a body of the catheter.

11. A method according to claim 9 wherein said irradiating the first amount of treated bacteria includes transmitting said light in an optical waveguide disposed within a wall of the catheter to said treated bacteria disposed near the distal portion.

* * * * *

UNITED STATES PATENT AND TRADEMARK OFFICE
CERTIFICATE OF CORRECTION

PATENT NO. : 11,135,445 B2
APPLICATION NO. : 16/277191
DATED : October 5, 2021
INVENTOR(S) : Daniela Vecchio et al.

It is certified that error appears in the above-identified patent and that said Letters Patent is hereby corrected as shown below:

In the Specification

Column 10, Line 11, "generation 12 could" should be --generation $I_2$ could--.

Column 11, Line 1, "Since 12 is" should be --Since $I_2$ is--.

Column 13, Line 22, "light atones as" should be --light alones as--.

Column 16, Line 50, "of 12 at" should be --of I2 at--.

Column 18, Line 61, "in vive" should be --in vivo--.

Column 22, Line 48, "for 102 called" should be --for $^1O_2$ called--.

Column 24, Line 54, "ad libium" should be --ad libitum--.

Column 29, Line 30, "the m vitro data" should be --the in vitro data--.

Signed and Sealed this
Fourth Day of January, 2022

Drew Hirshfeld
*Performing the Functions and Duties of the
Under Secretary of Commerce for Intellectual Property and
Director of the United States Patent and Trademark Office*